United States Patent
Ota et al.

(10) Patent No.: US 11,083,438 B2
(45) Date of Patent: Aug. 10, 2021

(54) ULTRASOUND DIAGNOSTIC APPARATUS, A TRANSMISSION CONDITION SETTING METHOD, AND PROGRAM

(71) Applicant: KONICA MINOLTA, INC., Tokyo (JP)

(72) Inventors: Kazushi Ota, Tokyo (JP); Akihiro Kawabata, Tokyo (JP); Tomohito Sakai, Kanagawa (JP); Takashi Sakai, Kanagawa (JP)

(73) Assignee: KONICA MINOLTA, INC., Tokyo (JP)

( * ) Notice: Subject to any disclaimer, the term of this patent is extended or adjusted under 35 U.S.C. 154(b) by 475 days.

(21) Appl. No.: 16/004,225

(22) Filed: Jun. 8, 2018

(65) Prior Publication Data
US 2019/0008481 A1 Jan. 10, 2019

(30) Foreign Application Priority Data
Jul. 10, 2017 (JP) .............................. JP2017-134944

(51) Int. Cl.
*A61B 8/08* (2006.01)
*A61B 8/00* (2006.01)
(Continued)

(52) U.S. Cl.
CPC ............ *A61B 8/5246* (2013.01); *A61B 8/463* (2013.01); *A61B 8/486* (2013.01); *A61B 8/5207* (2013.01); *A61B 8/546* (2013.01); *G01S 7/5202* (2013.01); *G01S 7/52046* (2013.01); *G01S 15/8915* (2013.01); *G01S 15/8988* (2013.01);
(Continued)

(58) Field of Classification Search
CPC ......... A61B 8/463; A61B 8/485; A61B 8/486; A61B 8/488; A61B 8/5207; A61B 8/5246; A61B 8/546; G01S 15/8915; G01S 15/8988; G01S 7/5202; G01S 7/52038; G01S 7/52046
See application file for complete search history.

(56) References Cited

U.S. PATENT DOCUMENTS

2004/0267119 A1* 12/2004 Adams ................ G01S 7/52046
600/437

FOREIGN PATENT DOCUMENTS

JP   H03261466 A   11/1991
JP   H07155324 A   6/1995

* cited by examiner

*Primary Examiner* — Michael T Rozanski
(74) *Attorney, Agent, or Firm* — Holtz, Holtz & Volek PC

(57) ABSTRACT

First transmission information in which an optimum transmitting voltage and a transmitting waveform are associated with each other for each display mode, and second transmission information in which a plurality of transmitting voltage candidates and pulse-width modulation transmitting waveforms that are pulse-width-modulation controlled to respectively correspond to the plurality of transmitting voltage candidates are associated with each other for each display mode are used to extract a maximum transmitting voltage candidate that does not exceed an optimum transmitting voltage of a first display mode from a plurality of transmitting voltage candidates included in the second transmission information of a second display mode so as to determine a common transmitting voltage used in common for the first display mode and the second display mode based on the optimum transmitting voltage of the first display mode and/or the maximum transmitting voltage candidate.

20 Claims, 6 Drawing Sheets

(51) Int. Cl.
*G01S 15/89* (2006.01)
*G01S 7/52* (2006.01)
(52) U.S. Cl.
CPC .............. *A61B 8/485* (2013.01); *A61B 8/488* (2013.01); *G01S 7/52038* (2013.01)

ULTRASOUND DIAGNOSTIC APPARATUS, A TRANSMISSION CONDITION SETTING METHOD, AND PROGRAM

CROSS REFERENCE TO RELATED APPLICATIONS

The entire disclosure of Japanese Patent Application No. 2017-134944 filed on Jul. 10, 2017, is incorporated herein by reference in its entirety.

BACKGROUND

Technological Field

The present invention relates to an ultrasound diagnostic apparatus, a transmission condition setting method, and a program that can simultaneously display ultrasound images of a plurality of display modes.

Description of Related Art

Conventionally, ultrasound diagnostic apparatuses are available in which ultrasound waves are emitted from an ultrasound probe into a subject, and the reflection waves are received and analyzed to inspect the inner side of the subject. Ultrasound diagnostic apparatuses can non-destructively and non-invasively examine subjects, and therefore are widely used in medical diagnosis.

In general, to generate ultrasound images having high image quality, it is desirable that the transmitting voltage supplied to the ultrasound probe be high as much as possible. When the transmitting voltage is excessively high, however, the temperature of the ultrasound probe (piezoelectric transducer) that transmits the ultrasound waves is increased, and/or the influence of transmitted ultrasound waves on the subject (living body) is increased, and in view of this, the transmitting voltage is preliminarily limited.

Incidentally, some ultrasound diagnostic apparatuses can generate ultrasound images of a plurality of display modes by changing the pulse width, wave number, amplitude and the like of the transmitting ultrasound beam (pulse wave). The suitable transmitting voltage differs among the display modes, and therefore, it is desirable to switch the transmitting voltage every time when the display mode is switched. The transmitting voltage can be switched by only switching the power source when a plurality of power systems are provided; however, with small-sized and space-saving ultrasound diagnostic apparatuses having only one power source system, it is difficult to switch the transmitting voltage appropriately for each display mode.

Techniques for solving the above-mentioned problems are disclosed in Japanese Patent Application Laid-Open No. H7-155324 and Japanese Patent Application Laid-Open No. H3-261466, for example. Japanese Patent Application Laid-Open No. H7-155324 discloses an ultrasound diagnostic apparatus that can smoothly and speedily perform display modes without changing the transmitting voltage by changing the transmission pulse duty for each display mode. In addition, Japanese Patent Application Laid-Open No. H3-261466 discloses an ultrasound diagnostic apparatus that can favorably control the transmission energy in real time even with a constant transmitting voltage by controlling the pulse width or duty ratio of the driving pulse output from a puller in a variable manner.

However, there is a demand for an ultrasound diagnostic apparatus that can acquire more favorable ultrasound images by further favorably controlling the transmitting voltage for each mode.

SUMMARY

An object of the embodiment of the present invention is to provide an ultrasound diagnostic apparatus, a transmission condition setting method, and a program that can acquire more favorable ultrasound images by favorably controlling the transmitting voltage for each mode.

To achieve the abovementioned object, an ultrasound diagnostic apparatus reflecting one aspect of the embodiment of the present invention is capable of simultaneously displaying ultrasound images of a plurality of display modes, the ultrasound diagnostic apparatus including a hardware processor configured to: store first transmission information in which an optimum transmitting voltage and a transmitting waveform are associated with each other for each display mode, and second transmission information in which a plurality of transmitting voltage candidates and pulse-width modulation transmitting waveforms that are pulse-width-modulation controlled so as to respectively correspond to the plurality of transmitting voltage candidates or a pulse-width modulation ratio that is a ratio of a section whose level is not 0 in a pulse-width modulation transmitting waveform are associated with each other for each display mode; and extract a maximum transmitting voltage candidate that does not exceed an optimum transmitting voltage of a first display mode of the plurality of display modes from a plurality of transmitting voltage candidates included in the second transmission information of a second display mode of the plurality of display modes so as to determine a common transmitting voltage used in common for the first display mode and the second display mode based on the optimum transmitting voltage of the first display mode and/or the maximum transmitting voltage candidate.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the embodiment of the present invention.

DETAILED DESCRIPTION OF EMBODIMENTS

Hereinafter, one or more embodiments of the embodiment of the present invention will be described with reference to the drawings. However, the scope of the invention is not limited to the disclosed embodiments.

[Configuration of Ultrasound Diagnostic Apparatus]

Figure 1:
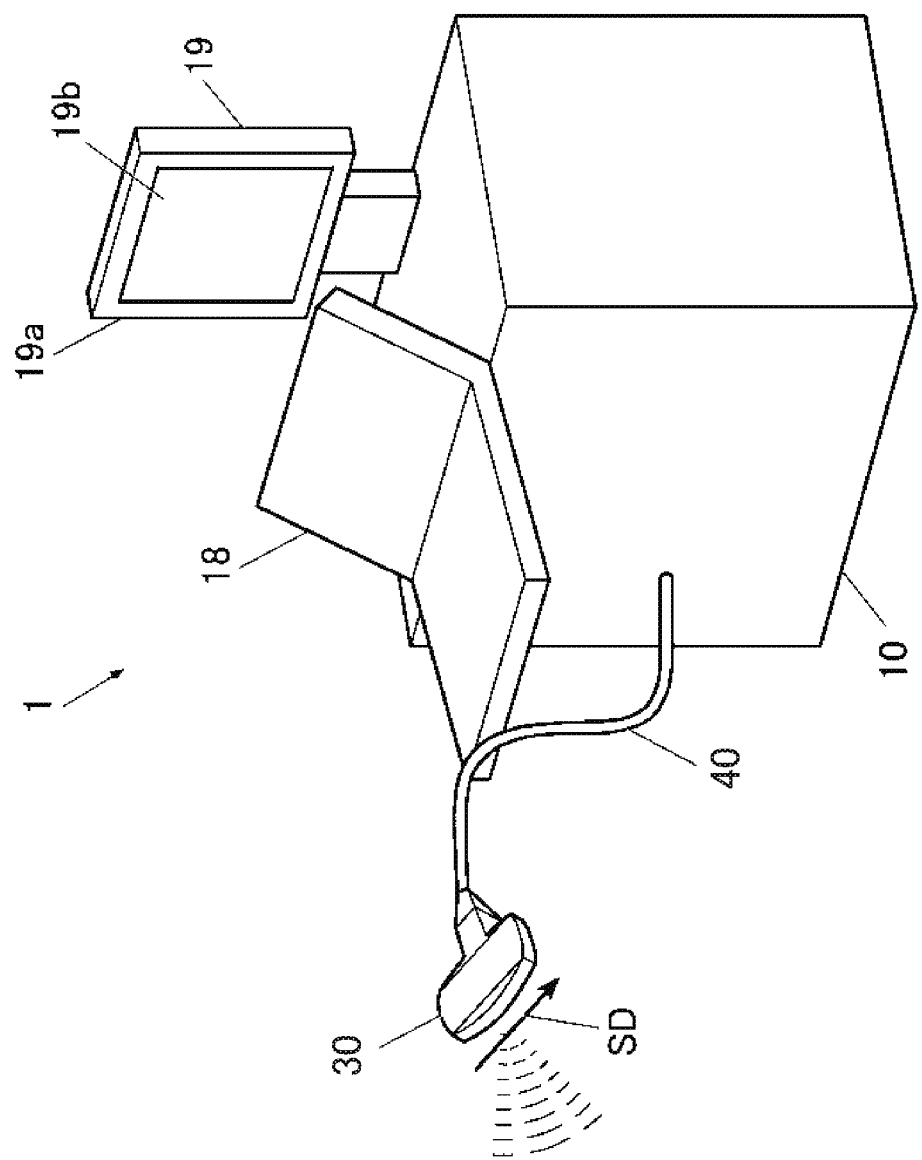
FIG. 1 illustrates a schematic configuration of an ultrasound diagnostic apparatus according to an embodiment of the present invention.
Figure 2:
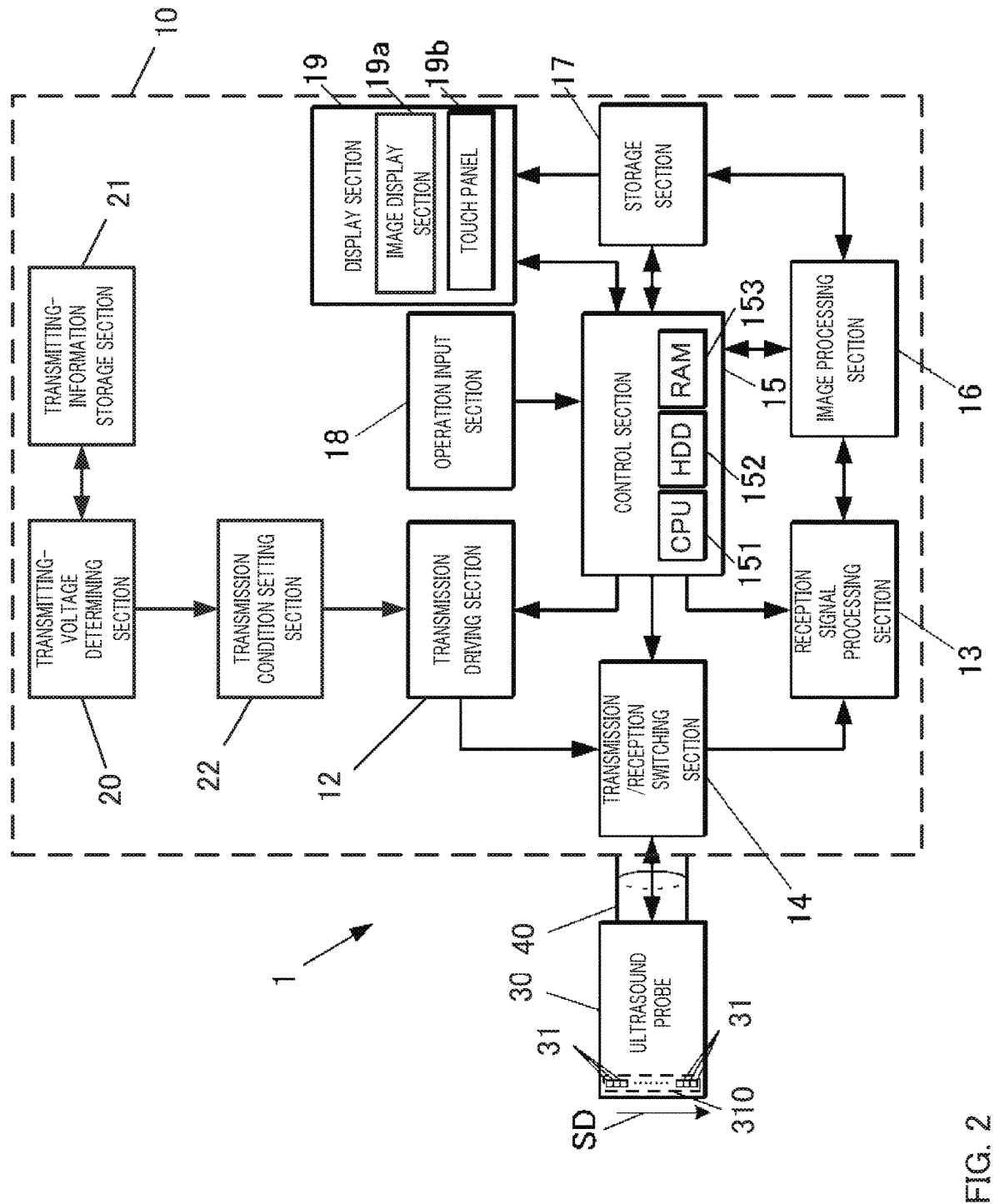
FIG. 2 is a block diagram illustrating a configuration of main functions of the ultrasound diagnostic apparatus.

FIG. 1 illustrates a schematic configuration of ultrasound diagnostic apparatus 1 according to the embodiment of the embodiment of the present invention. FIG. 2 is a block diagram illustrating a configuration of main functions of ultrasound diagnostic apparatus 1.

As illustrated in FIG. 1, ultrasound diagnostic apparatus 1 includes ultrasound diagnostic apparatus main body 10, and ultrasound probe 30 connected with ultrasound diagnostic apparatus main body 10 through cable 40. Ultrasound diagnostic apparatus main body 10 is provided with operation input section 18, and display section 19 including image display section 19a and touch panel 19b.

On the basis of an inputting operation of the operator using operation input section 18 that is an input device such as a keyboard and a mouse, and/or a touching operation of the operator on touch panel 19b of display section 19, control section 15 of ultrasound diagnostic apparatus main body 10 outputs a driving signal to ultrasound probe 30 to cause ultrasound probe 30 to output ultrasound waves, and receives a reception signal according to reception of ultrasound waves from ultrasound probe 30 so as to perform various processes, and, as necessary, cause image display section 19a to display the result.

As illustrated in FIG. 2, ultrasound diagnostic apparatus main body 10 includes transmitting-voltage determining section 20, transmitting-information storage section 21, transmission condition setting section 22, transmission driving section 12, reception signal processing section 13, transmission/reception switching section 14, control section 15, image processing section 16, storage section 17, operation input section 18, display section 19, and the like.

With reference to transmitting-information storage section 21, transmitting-voltage determining section 20 determines a voltage (transmitting voltage) of a pulse signal (driving signal) to be supplied to ultrasound probe 30. Transmitting-information storage section 21 stores information that is used by transmitting-voltage determining section 20 for determining a transmitting voltage. Transmission condition setting section 22 sets a transmission condition based on predetermined information stored in transmitting-information storage section 21, and a transmitting voltage determined by transmitting-voltage determining section 20. It is to be noted that in the present invention, the "transmission condition" means a setting condition for controlling ultrasound waves that are transmitted from ultrasound probe 30, and the setting condition includes preliminarily set predetermined information on a transmission opening, a focusing position, a transmission interval and the like, and a transmitting voltage and a transmitting waveform of a driving signal, for example. Details of the transmission condition setting method of transmission condition setting section 22 and transmitting-voltage determining section 20 are described later.

Transmission driving section 12 outputs a pulse signal (driving signal) to be supplied to ultrasound probe 30 in accordance with a transmission condition set by transmission condition setting section 22. For example, transmission driving section 12 includes a clock generating circuit, a pulse generating circuit, a pulse width setting section, and a delay circuit. The clock generating circuit is a circuit that generates a clock signal for determining the transmission timing and/or the transmission frequency of a pulse signal. The pulse generating circuit is a circuit that generates a rectangular pulse of a transmitting voltage based on a transmission condition. The pulse width setting section sets the pulse width of a rectangular pulse that is output from the pulse generating circuit based on a transmitting waveform included in a transmission condition. Before or after being input to the pulse width setting section, the rectangular pulse generated by the pulse generating circuit is separated to wiring paths for respective transducers 31 of ultrasound probe 30. The delay circuit is a circuit that outputs the generated rectangular pulse with delay by the delay time set for each of the wiring paths in accordance with the timings of transmitting the generated rectangular pulse to transducers 31.

While the pulse signal generated by transmission driving section 12 is a rectangular pulse in the above mentioned description, transmission driving section 12 may generate pulse signals other than a rectangular wave (e.g. a sine wave, a triangle wave and the like).

In addition, although not illustrated in the drawings, transmission driving section 12 includes a power source of one system, or is connected with a power source of one system so as to generate a driving signal based on the power source.

Reception signal processing section 13 is a circuit that acquires a reception signal input from ultrasound probe 30 under the control of control section 15. Reception signal processing section 13 includes, for example, an amplifier, an A/D conversion circuit, and a phasing addition circuit. The amplifier is a circuit that amplifies, by a preliminarily set predetermined amplification factor, reception signals in accordance with the ultrasound waves received by transducers 31 of ultrasound probe 30. The A/D conversion circuit is a circuit that converts an amplified reception signal into digital data based on a predetermined sampling frequency. The phasing addition circuit is a circuit that generates sound ray data by adjusting the phase of an A/D converted reception signal by adding a delay time for each wiring path corresponding to each transducer 31, and by adding the signals (phasing addition).

Under the control of control section 15, transmission/reception switching section 14 performs a switching operation so as to emit ultrasound waves from transducer 31 by causing driving signal transmission driving section 12 to send ultrasound waves to transducer 31, and so as to acquire a signal representing ultrasound waves emitted from transducer 31 by causing reception signal processing section 13 to output a reception signal.

Control section 15 includes CPU 151 (Central Processing Unit), HDD 152 (Hard Disk Drive), RAM 153 (Random Access Memory) and the like. CPU 151 reads various programs stored in HDD 152 and develops the programs in RAM 153 so as to control the operations of the components of ultrasound diagnostic apparatus 1 in accordance with the developed program. HDD 152 stores image files generated by ultrasound diagnostic apparatus 1, various setting data, various processing programs, control programs for operating ultrasound diagnostic apparatus 1, and the like. Other than HDD 152, the above-mentioned programs and setting data may be stored in an auxiliary storage apparatus using a nonvolatile memory such as a flash memory in a rewritable manner. RAM 153, which is a volatile memory such as a SRAM and a DRAM for example, provides a working memory space in CPU 151, and stores temporarily data.

Image processing section 16 performs arithmetic processing for generating an ultrasound image based on received data of ultrasound waves. The ultrasound image includes image data to be displayed in real time on display section 19 and moving image data of a series of the image data, snap-shot still picture data and the like. It is to be noted that the arithmetic processing may be performed by CPU 151.

Storage section 17 is, for example, a volatile memory such as a DRAM (Dynamic Random Access Memory). Alternatively, storage section 17 may be a nonvolatile memory capable of high-speed rewriting. Storage section 17 stores, in a frame unit, ultrasound image data for real-time displaying processed in image processing section 16. The image data stored in storage section 17 is read under the control of control section 15 so as to be transmitted to image display section 19a, and/or to be output from ultrasound diagnostic apparatus 1 through the communication section (not illustrated). At this time, in the case where the display system of image display section 19a is a television system, the data can be output after the scanning format is converted with a DSC (Digital Signal Converter: not illustrated) provided between storage section 17 and image display section 19a.

Operation input section 18, which includes a push button switch, a keyboard, a mouse, a trackball, or a combination thereof, converts an operator's inputting operation into an operation signal, and outputs the signal to control section 15.

Image display section 19a of display section 19 includes a display screen of an LCD (Liquid Crystal Display), an organic EL (Electro-Luminescence) display, an inorganic EL display, a plasma display, or a CRT (Cathode Ray Tube) display, and, a driving section thereof. Image display section 19a generates a driving signal for the display screen (each pixel) in accordance with a control signal output from CPU 151, and/or image data generated at image processing section 16, and displays on the display screen a status and a menu according to an ultrasound diagnosis, and, measurement data of an ultrasound image based on received ultrasound waves and the like.

Touch panel 19b of display section 19 is a capacitive touch panel disposed on the display screen of image display section 19a. When an operator's finger or the like touches the surface of touch panel 19b, touch panel 19b detects the touch based on a change in capacitance between an inner conducting film and the surface, and outputs to control section 15 a signal representing the position of the detected touch as an operation signal. It is to be noted that touch panel 19b is not limited to the capacitive touch panel, and touch panel 19b may be of a resistance film type, an electromagnetic induction type or the like.

Each of operation input section 18 and display section 19 may be provided integrally with the housing of ultrasound diagnostic apparatus main body 10, or may be externally attached thereto through a USB cable and the like. In addition, in the case where ultrasound diagnostic apparatus main body 10 is provided with an operation input terminal and/or a display output terminal, peripheral devices may be connected to the terminals conventional operating and displaying.

Ultrasound probe 30 functions as an acoustic sensor that transmits (emits) ultrasound waves (e.g. about 1 to 30 MHz) to a subject such as a living body, and receives reflection waves (echo) of the transmitted ultrasound waves reflected by the subject so as to and converts the reflection waves into an electric signal. Ultrasound probe 30 includes transducer arrangement 310 that is an arrangement of a plurality of transducers 31 for transmitting and receiving ultrasound waves.

Transducer arrangement 310 is an arrangement of a plurality of transducers 31, each of which includes a piezoelectric element including a piezoelectric body and electrodes provided at both ends of the piezoelectric body where an electric charge appears in response to deformation (expansion and contraction) of the piezoelectric body. The piezoelectric body is deformed in accordance with an electric field generated at each piezoelectric body when a voltage pulse (pulse signal) is supplied to transducer 31, and thus ultrasound waves are transmitted. In addition, when ultrasound waves of a predetermined frequency band impinge on transducer 31, the thickness of the piezoelectric body is varied (vibrated) by the sound pressure of the ultrasound waves, and an electric charge in accordance with the amount of the variation appears at both ends of the piezoelectric body in the direction in which the thickness varies, whereby an electric charge corresponding to the electric charge is induced at the electrodes at the both ends of the piezoelectric element.

Transducer arrangement 310 of ultrasound probe 30 of the present embodiment includes about one hundred to a few hundreds of transducers 31 that are one-dimensionally arranged in a predetermined transducer arrangement direction. Alternatively, transducers 31 may be two-dimensionally arranged in a direction orthogonal to the transducer arrangement direction. In addition, the number of transducers 31 may be arbitrarily set. Ultrasound probe 30 of the present embodiment transmits ultrasound waves from a pair of successive transducers 31 of the about one hundred to a few hundreds of transducers 31 based on a pulse signal from transmission driving section 12. Then, scanning is performed in scanning direction SD that is parallel to the transducer arrangement direction by shifting a group of transducers 31 for transmitting ultrasound waves by a distance corresponding to a predetermined number of transducers 31 in the transducer arrangement direction every time when ultrasound waves are generated. In addition, the present embodiment employs ultrasound probe 30 of linear electronic scanning type in which the transmission directions of ultrasound waves transmitted at different timings are parallel to each other. It is to be noted that ultrasound probe 30 may be of an electronic scanning type such as a sector electronic scanning type and a convex electronic scanning type, or a machine scanning type such as a linear scanning type, a sector scanning type, an arc scanning type, and a radial scanning type. In addition, the band width of the reception frequency of the ultrasound waves of ultrasound probe 30 may be arbitrarily set.

In addition, ultrasound diagnostic apparatus 1 may have a configuration in which any of a plurality of different ultrasound probes 30 are connected with ultrasound diagnostic apparatus main body 10 in accordance with the diagnosis object.

A connector (not illustrated) for connection with ultrasound diagnostic apparatus main body 10 is disposed at one end of cable 40, and ultrasound probe 30 can be attached to or detached from ultrasound diagnostic apparatus main body 10 with cable 40.

[Operation of Ultrasound Diagnostic Apparatus]

Now, an operation of ultrasound diagnostic apparatus 1 is described. Ultrasound diagnostic apparatus 1 allows for selection of display modes of multiple types of the ultrasound image. The display modes of ultrasound diagnostic apparatus 1 include, for example, single modes such as B mode, color-Doppler mode, pulse-Doppler mode (Doppler mode), M (Motion) mode, E (Elastography) mode, and Mc mode in which color Doppler is superimposed on M mode, and combined modes composed of a combination of multiple modes. In the present embodiment, the combined mode includes modes composed of two modes (Duplex mode) and modes composed of three modes (Triplex mode). Examples of the Duplex mode include Bc mode in which a color-Doppler mode image is superimposed on a B mode image, BD mode in which a B mode image and a pulse-Doppler mode image are simultaneously displayed, a BM mode in which a B mode image and a M mode image are simultaneously displayed, and Be mode in which a B mode image and an E mode image are simultaneously displayed. Examples of the Triplex mode include BcD mode in which a color-Doppler mode image superimposed on a B mode image and a pulse-Doppler mode image are simultaneously displayed, and BcMc mode in which a color-Doppler mode image superimposed on a B mode image and an Mc mode image are simultaneously displayed.

<Single Mode>

Ultrasound diagnostic apparatus 1 operates as follows when a single mode is selected, for example. A display mode is selected by operation input section 18. Below, an example case where B mode is selected as the single mode is described.

Transmitting-voltage determining section 20 determines a transmitting voltage corresponding to B mode based on information preliminarily stored in transmitting-information storage section 21. It is to be noted that the information preliminarily stored in transmitting-information storage section 21 is information (hereinafter referred to as transmission information) in which an optimum transmitting voltage for each display mode, and a transmitting waveform corresponding to that transmitting voltage are preliminarily associated with each other.

Transmission condition setting section 22 sets a determined transmission condition. Further, transmission driving section 12 outputs a driving signal to ultrasound probe 30 in accordance with the set transmission condition.

Ultrasound probe 30 transmits ultrasound waves based on the driving signal, and receives an echo reflected in a subject. Ultrasound probe 30 generates a reception signal based on the received echo, and outputs the signal to reception signal processing section 13. Reception signal processing section 13 generates sound ray data based on the reception signal, and outputs the sound ray data to image processing section 16. Image processing section 16 generates an ultrasound image based on the sound ray data. The generated ultrasound image is displayed on display section 19. It is to be noted that transmission/reception switching section 14 appropriately switches output of a driving signal and input of a reception signal between ultrasound diagnostic apparatus main body 10 and ultrasound probe 30.

<History of the Invention>

Now, after the history of the embodiment of the present invention is described, an operation of a combined mode is described. While Bc mode in which B mode and color-Doppler mode are combined is selected as a combined mode in the following description of the history, the same applies to the cases where other combined modes are selected. It is to be noted that Bc mode is a mode in which a B mode image and a color Doppler image obtained by alternately switching a B mode transmission cycle and a color Doppler transmission cycle in a short time are synthesized and displayed in real time.

In general, in B mode, a wide-band signal capable of achieving high resolution, or in other words, a driving signal of a short pulse wave, is used for the purpose of generating high image quality image. On the other hand, in color-Doppler mode, a signal of a specific frequency band (narrowband signal), or in other words, a driving signal of a long pulse wave, is used since color-Doppler mode is a mode for obtaining a blood flow and/or a blood flow spectrum based mainly on the phase of a reception signal. A long pulse wave driving signal is used also in the case where pulse-Doppler mode and E mode are used, as in color-Doppler mode.

Here, in order to generate an ultrasound image of high image quality, that is, in order to improve the S/N ratio of a reception signal, it is desirable to increase the amplitude of the pulse to be applied to the piezoelectric transducer by increasing the voltage (transmitting voltage) of the driving signal.

However, in view of reducing the influence of high ultrasound wave energy on a living body, an acoustic output (ultrasound wave output) of transmitted ultrasound waves emitted from an ultrasound probe is regulated in accordance with modes. The energy of transmitted ultrasound waves is determined based on the frequency (pulse length) and the voltage amplitude of the driving signal, and therefore, in pulse-Doppler mode and color-Doppler mode in which a driving signal of long pulse waves is used, it is necessary to lower the transmitting voltage in comparison with B mode. Accordingly, in a combined mode in which images of different modes are switched at high speed and simultaneously displayed, the transmitting voltage is required to be changed at high speed for each cycle.

For example, an ultrasound diagnostic apparatus including a plurality of power systems can change the transmitting voltage for each cycle by a switching control for switching the power source to the power source corresponding to the mode between B mode cycle and other mode cycles. However, this method cannot be employed in the present embodiment since the present embodiment includes only one power source system. An example of a method for changing a transmitting voltage for each cycle by one power source system is a method in which a transmitting voltage generated by the pulse generating circuit of transmission driving section 12 is changed for each cycle to generate transmitting voltages corresponding to respective modes.

When such a method is employed, however, heat is generated at transducer 31 due to high-speed pulse generation, and as a result, the surface temperature of ultrasound probe 30 is raised, or the time response of pulse generation is delayed, making it difficult to perform the real-time switching of the transmitting voltage for each cycle in some situation. A possible way for solving the above-mentioned problem might be a method in which a common transmitting voltage (hereinafter referred to as common transmitting voltage) is generated without changing the transmitting voltage for each mode even in a Duplex mode.

As described above, for the regulation, the transmitting voltage of color-Doppler mode is required to be lowered in comparison with the transmitting voltage of B mode, and therefore, when the same transmitting voltage (common transmitting voltage) is to be used between B mode and color-Doppler mode, the voltage is required to be set to the voltage of color-Doppler mode that is lower than that of B mode. However, when a B mode image is generated with the transmitting voltage corresponding to color-Doppler mode, the S/N ratio is reduced and the image quality of B mode image is degraded in some situation.

Under such circumstances, an object of ultrasound diagnostic apparatus 1 according to the present embodiment is to generate an ultrasound image having a suitable image quality even when a combined mode display is performed with a common transmitting voltage.

<Combined Mode (Duplex Mode)>

Now an operation of ultrasound diagnostic apparatus 1 in a Duplex mode of the combined mode is described. When Bc mode is selected by operation input section 18 for example, a transmission condition corresponding to Bc mode is set by transmitting-voltage determining section 20. A case where Bc mode is selected as Duplex mode is described below.

In Bc mode, as in the single mode, transmitting-voltage determining section 20 determines a transmission condition based on transmission information corresponding to Bc mode preliminarily stored in transmitting-information storage section 21. It should be noted that, in the combined mode, transmission information that is different from that of the single mode is used.

In order to generate an ultrasound image having suitable image quality even when a combined mode display is performed with a common transmitting voltage, it is desirable that the common transmitting voltage that is used in both B mode cycle and color-Doppler mode cycle in Bc mode be higher than the transmitting voltage optimum for color-Doppler mode; however, the acoustic output of the ultrasound waves in color-Doppler mode should be controlled so as not to exceed the regulation value in color-Doppler mode. In order to increase the transmitting voltage without increasing the acoustic output of the ultrasound waves, a pulse-width modulation (PWM: Pulse Width Modulation) control is applied for color-Doppler mode in ultrasound diagnostic apparatus 1 according to the present embodiment.

In the PWM control, the output value is controlled by changing the waveform determined based on the PWM ratio while maintaining the voltage at a constant value. That is, transmitting-voltage determining section 20 can increase the transmitting voltage without increasing the acoustic output of the ultrasound waves in color-Doppler mode by use of possible candidates for transmitting voltage and PWM waveforms corresponding to respective transmitting voltages as transmission information of color-Doppler mode. Here, the PWM ratio is a numerical value that indicates the ratio of the section whose level is not 0, to the main pulse. In addition, the PWM waveform is a waveform obtained by applying the PWM ratio to the waveform of the main pulse. That is, in transmitting-information storage section 21, a plurality of transmitting voltage candidates in color-Doppler mode and PWM waveforms corresponding to respective transmitting voltage candidates are associated with each other and stored in a table format for example.

In the following description, the transmission information to which the PWM control has been applied is referred to as PWM transmission information so as to be discriminated from transmission information to which the PWM control is not applied. It is to be noted that the transmission information to which the PWM control is not applied is an example of the first transmission information of the embodiment of the present invention, and the PWM transmission information is an example of the second transmission information of the embodiment of the present invention. While the plurality of transmitting voltage candidates and PWM waveforms corresponding to respective transmitting voltage candidates are associated with each other and stored in transmitting-information storage section 21 as the PWM transmission information in the above description, the PWM ratio may be stored in place of the PWM waveform.

Transmitting-voltage determining section 20 reads the PWM transmission information corresponding to color-Doppler mode from transmitting-information storage section 21, selects as high transmitting voltage candidate as possible from among the plurality of transmitting voltage candidates, and determines the selected transmitting voltage candidate and the transmitting waveform corresponding to the selected transmitting voltage candidate to be the transmission condition, whereby transmitting-voltage determining section 20 can set the common transmitting voltage that is used in Bc mode to as high transmitting voltage as possible.

Then, transmission condition setting section 22 sets the transmission condition determined by transmitting-voltage determining section 20, and transmission driving section 12 outputs a driving signal in accordance with the set transmission condition. Here, transmission driving section 12 generates a B mode transmission pulse in the B mode transmission cycle, and a color-Doppler transmission pulse in the color Doppler cycle. The transmission condition setting method in a Duplex mode is elaborated later.

Ultrasound probe 30 transmits ultrasound waves based on the driving signal, and receives an echo reflected in a subject. Ultrasound probe 30 generates a reception signal based on the received echo, and outputs the signal to reception signal processing section 13. Reception signal processing section 13 generates sound ray data based on the reception signal, and outputs the sound ray data to image processing section 16. Image processing section 16 generates an ultrasound image based on the sound ray data. The generated ultrasound image is displayed on display section 19. It is to be noted that transmission/reception switching section 14 appropriately switches output of a driving signal and input of a reception signal between ultrasound diagnostic apparatus main body 10 and ultrasound probe 30.

It is to be noted that the gain of B mode to which the PWM control has not been applied may be compensated when image processing section 16 generates an ultrasound image. To be more specific, by multiplying the gain of B mode by (optimum transmitting voltage of B mode)/(common transmitting voltage) (this multiplying factor is hereinafter referred to as α-times), the gain of B mode which is low due to employment of a common transmitting voltage can be compensated. Note that it corresponds to addition of a value obtained by converting α-times into decibel (dB) in terms of the gain compensation amount for a signal subjected to a Log-compression, since a B mode image is normally generated by Log-compression of the reception signal in image processing section 16. Alternatively, in the case where B mode is high harmonic imaging by THI (Tissue Harmonic Imaging), the gain of B mode may be multiplied by the square of a (after Log-compression, a doubled value of a value obtained by decibel-converting "α-times" is added). Alternatively, the gain compensation amount may be determined by other functions in which (optimum transmitting voltage of B mode) and (common transmitting voltage) are the input regardless of whether THI or not. With this configuration, degradation in image quality of B mode can be reduced.

<Transmission Condition Setting Method (Duplex Mode)>

Figure 3:
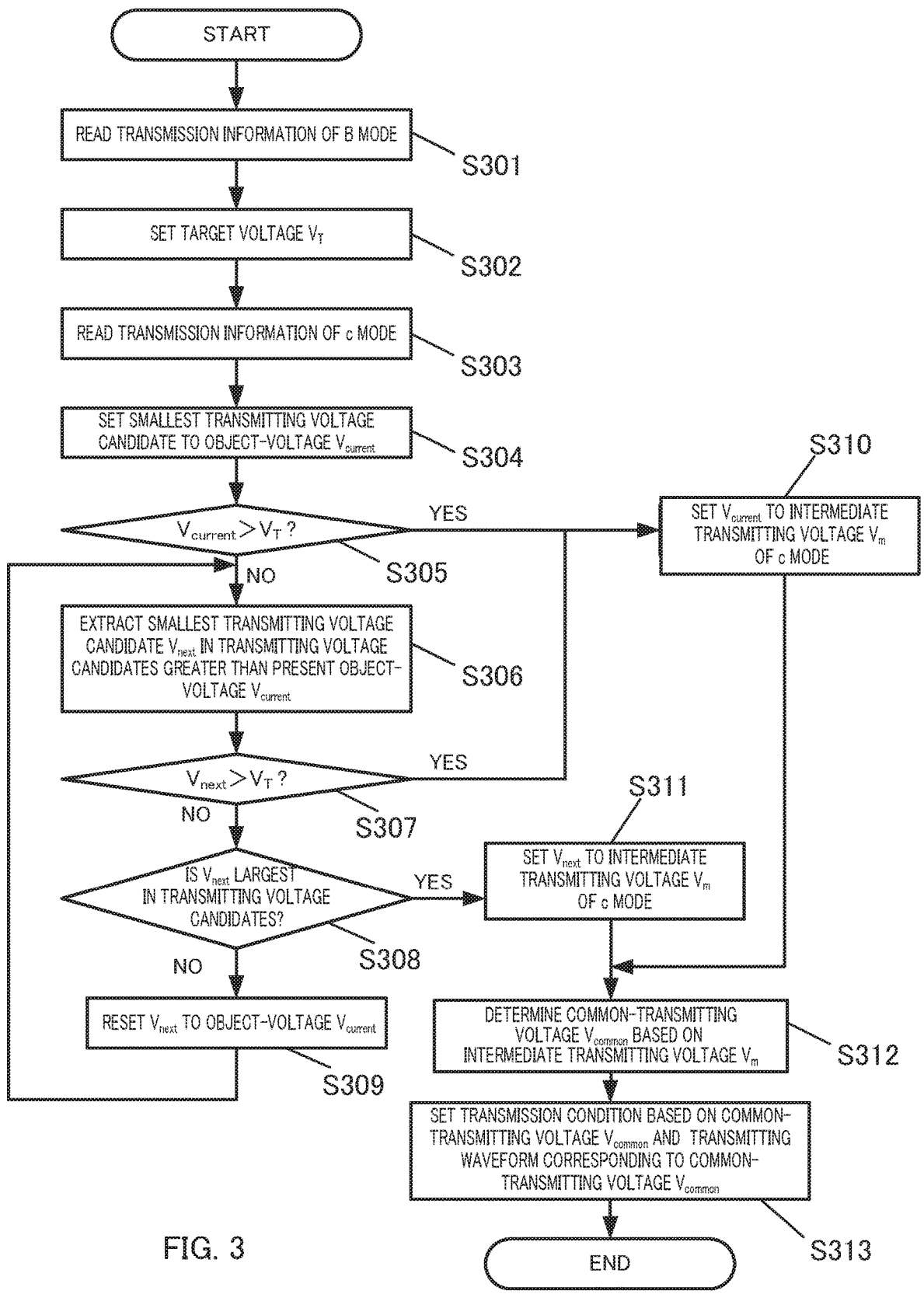
FIG. 3 is a flowchart of a transmission condition setting method in a Duplex mode.

Now the transmission condition setting method in a Duplex mode is described. FIG. 3 is a flowchart of a transmission condition setting method in a Duplex mode.

At step S301, transmitting-voltage determining section 20 reads transmission information corresponding to B mode, that is, information including the optimum transmitting voltage of B mode, and the transmitting waveform corresponding to the transmitting voltage from transmitting-information storage section 21.

At step S302, transmitting-voltage determining section 20 sets the optimum transmitting voltage of B mode to target voltage $V_T$.

At step S303, transmitting-voltage determining section 20 reads the PWM transmission information corresponding to color-Doppler mode (hereinafter referred to as c mode) from transmitting-information storage section 21. As described above, the PWM transmission information corresponding to c mode includes the plurality of transmitting voltage candidates, and PWM waveforms corresponding to respective transmitting voltage candidates in a table format, for example.

At step S304, transmitting-voltage determining section 20 sets the processing object to the smallest transmitting voltage candidate (minimum voltage) in the plurality of transmitting voltage candidates included in the PWM transmission information corresponding to c mode read at step S303. The transmitting voltage candidate serving as the processing object is referred to as object-voltage $V_{current}$.

At step S305, transmitting-voltage determining section 20 compares object-voltage $V_{current}$ and target voltage $V_T$ set at step S302. When the object-voltage $V_{current}$ is larger than target voltage $V_T$ (step S305: YES), the process is advanced to step S310, and when the object-voltage $V_{current}$ is not larger than target voltage $V_T$ (step S305: NO), the process is advanced to step S306.

At step S306, transmitting-voltage determining section 20 extracts the smallest transmitting voltage candidate $V_{next}$ in the transmitting voltage candidates greater than the present object-voltage $V_{current}$ from among the plurality of transmitting voltage candidates included in the PWM transmission information corresponding to c mode read at step S303.

At step S307, transmitting-voltage determining section 20 compares $V_{next}$ extracted at step S306 and target voltage $V_T$. When $V_{next}$ is larger than target voltage $V_T$ (step S307: YES), the process is advanced to step S310, and when $V_{next}$ is not larger than target voltage $V_T$ (step S307: NO), the process is advanced to step S308.

At step S308, transmitting-voltage determining section 20 determines whether $V_{next}$ is the largest transmitting voltage candidate in the plurality of transmitting voltage candidates included in the PWM transmission information corresponding to c mode read at step S303. When $V_{next}$ is the largest transmitting voltage candidate in the plurality of transmitting voltage candidates (step S308: YES), the process is advanced to step S311, and when $V_{next}$ is not the largest transmitting voltage candidate in the plurality of transmitting voltage candidates (step S308: NO), the process is advanced to step S309.

At step S309, transmitting-voltage determining section 20 resets object-voltage $V_{current}$ to $V_{next}$ and the process is returned to step S306.

At step S310, transmitting-voltage determining section 20 sets $V_{current}$ to intermediate transmitting voltage $V_m$ in c mode. Intermediate transmitting voltage $V_m$ in c mode is a temporary transmitting voltage that is used for determining common-transmitting voltage $V_{common}$ in Bc mode.

At step S311, transmitting-voltage determining section 20 sets $V_{next}$ to intermediate transmitting voltage $V_m$ in c mode.

At step S312, transmitting-voltage determining section 20 determines common-transmitting voltage $V_{common}$ based on target voltage $V_T$ and/or intermediate transmitting voltage $V_m$.

Examples of the method of determining common-transmitting voltage $V_{common}$ based on target voltage $V_T$ and/or intermediate transmitting voltage $V_m$ include the following methods. In the first exemplary method, common-transmitting voltage $V_{common}$ is set to smaller one of target voltage $V_T$ and c mode intermediate transmitting voltage $V_m$. Here, the case where target voltage $V_T$ is smaller corresponds to the case where object-voltage $V_{current}$ is greater than target voltage $V_T$ when compared at step S305. The second exemplary method is a method of optimizing common-transmitting voltage $V_{common}$. The optimization condition is that the acoustic output of the ultrasound waves in each of B mode and c mode does not exceed the regulation value of each mode and the voltage is as high as possible. This condition is referred to as Condition 1 in the following description.

The common-transmitting voltage $V_{common}$ may be optimized based on target voltage $V_T$, intermediate transmitting voltage $V_m$, transmission interval between B mode and c mode, the number of transmission B mode and c mode per unit time, and the like, for example.

For example, common-transmitting voltage $V_{common}$ may be the largest transmitting voltage in common-transmitting voltages $V_{common}$ meeting Condition 1 determined by searching. Alternatively, common-transmitting voltage $V_{common}$ may be the largest in transmitting voltage meeting Condition 1 in possible candidates for transmitting voltage prepared in advance through an experiment and the like and stored in transmitting-information storage section 21 and the like.

Common-transmitting voltage $V_{common}$ that meets Condition 1 can be determined by searching a parameter where common-transmitting voltage $V_{common}$ is maximized while adjusting the transmission interval and the number of transmission of per unit time of B mode, and the transmission interval and the transmission frequency per unit time of c mode, for example.

To be more specific, common-transmitting voltage $V_{common}$ that meets Condition 1 can be determined by the following methods, for example. The first exemplary method is a method of actually measuring the acoustic output of the ultrasound waves and the temperature rise at the probe surface by use of a sensor which can be mounted in a probe or the like.

Specifically, transmitting-information storage section 21 stores a preliminarily obtained measurement result of the acoustic output of the ultrasound waves and the temperature rise at the probe surface that is obtained by repeating transmission with the waveform of B mode, at the transmitting voltage of B mode and the transmission interval of B mode and by the transmission frequency per unit time of B mode, and transmission with the PWM waveform of c mode at the transmitting voltage of c mode and the transmission interval of c mode, and by the transmission frequency per unit time of c mode. The measurement result of the acoustic output of the ultrasound waves and the temperature rise at the probe surface is stored for each possible combination of the transmitting voltage of B mode, the transmission interval of B mode, the transmission frequency per unit time of B mode, the waveform of B mode, the PWM waveform of c mode corresponding to transmitting voltage, the transmission interval of c mode, the transmission frequency per unit time of c mode, and the PWM waveform of c mode.

When target voltage $V_T$ and intermediate transmitting voltage $V_m$ are determined in the steps before step S312, transmitting-voltage determining section 20 acquires the acoustic output of the ultrasound waves and the temperature rise at the probe surface from transmitting-information storage section 21 by setting the transmitting voltage of B mode to target voltage $V_T$, and the transmitting voltage of c mode to intermediate transmitting voltage $V_m$, and by using the transmission interval of B mode, the transmission frequency per unit time of B mode, the waveform of B mode, the transmission interval of c mode, the transmission frequency per unit time of c mode, and intermediate transmitting voltage $V_m$ corresponding to the PWM waveform of c mode of this case.

Then, transmitting-voltage determining section 20 temporarily sets the initial value of common-transmitting voltage $V_{common}$, and, by use of common-transmitting voltage $V_{common}$, repeats transmission with the waveform of B mode, at the transmission interval of B mode and by the transmission frequency per unit time of B mode and transmission with the PWM waveform of c mode at the transmission interval of c mode and by the transmission frequency per unit time of c mode, so as to perform adjustment such that common-transmitting voltage $V_{common}$ is maximized in the range below the value acquired from transmitting-information storage section 21 while measuring the acoustic output of the ultrasound waves and the temperature rise at the probe surface with the sensor. For example, the initial value of common-transmitting voltage $V_{common}$ may be smaller one of target voltage $V_T$ and c mode intermediate transmitting voltage $V_m$.

The second exemplary method is a method of calculating common-transmitting voltage $V_{common}$ by modelling the acoustic output of the ultrasound waves and the temperature rise at the probe surface.

The acoustic output of the ultrasound waves and the temperature rise at the probe surface increase as the transmitting voltage increases and as the transmission interval decreases. In addition, as the pulse length of the waveform increases, the acoustic output of the ultrasound waves and the temperature rise at the probe surface increase. In other words, the acoustic output of the ultrasound waves and the temperature rise at the probe surface are affected by the transmitting voltage, the transmission interval, and the waveform. By utilizing this, common-transmitting voltage $V_{common}$ is calculated in the second exemplary method.

First, the relationship between the transmitting voltage, and the acoustic output of the ultrasound waves and the temperature rise at the probe surface, and the relationship between the transmission interval, and the acoustic output of the ultrasound waves and the temperature rise at the probe surface are modelled for each waveform and stored in transmitting-information storage section 21.

In addition, for example, when a B mode transmission cycle and a c mode transmission cycle are alternately switched in a short time in a combined mode, the relationship between the transmission frequency per unit time and the transmission interval of these modes, and the combined ratio thereof, and the acoustic output of the ultrasound waves and the temperature rise at the probe surface is also modelled, and stored in transmitting-information storage section 21. For example, as the proportion of the transmission period of in a mode in which the acoustic output of the ultrasound waves and the temperature rise at the probe surface increases, the acoustic output of the ultrasound waves and the temperature rise at the probe surface of the combined mode increase.

When target voltage $V_T$ and intermediate transmitting voltage $V_m$ are determined in the steps before step S312, transmitting-voltage determining section 20 calculates, with reference to the model stored in transmitting-information storage section 21, the acoustic output of the ultrasound waves and the temperature rise at the probe surface that is obtained when transmission at the transmitting voltage of B mode and at the transmission interval of B mode by the transmission frequency per unit time of B mode, with the waveform of B mode, and transmission with the waveform of c mode at the interval of intermediate transmitting voltage $V_m$ of c mode by the transmission frequency per unit time of c mode are repeated, and transmitting-voltage determining section 20 uses the result of the calculation as a reference.

With reference to the model stored in transmitting-information storage section 21, transmitting-voltage determining section 20 can calculate the acoustic output of the ultrasound waves and the temperature rise at the probe surface of the case where, by use of common-transmitting voltage $V_{common}$, transmission with the waveform of B mode at the transmission interval of B mode and by the transmission frequency per unit time of B mode, and transmission with the PWM waveform of c mode at the transmission interval of c mode and by the transmission frequency per unit time of c mode are repeated. In other words, transmitting-voltage determining section 20 calculates the acoustic output of the ultrasound waves and the temperature rise at the probe surface by changing common-transmitting voltage $V_{common}$, so as to obtain common-transmitting voltage $V_{common}$ that does not exceed the reference by searching. It is to be noted that transmitting-voltage determining section 20 may obtain common-transmitting voltage from among possible candidates for transmitting voltage prepared in advance by searching the maximum transmitting voltage that meets Condition 1.

At step S313, transmission condition setting section 22 sets the transmission condition based on common-transmitting voltage $V_{common}$ determined at step S312 and the transmitting waveform of each mode corresponding to common-transmitting voltage $V_{common}$. That is, on the basis of the transmission information of each mode read from transmitting-information storage section 21, transmission condition setting section 22 sets the transmitting waveform in the B mode cycle to the transmitting waveform of B mode corresponding to common-transmitting voltage $V_{common}$, and sets the transmitting waveform in the c mode cycle to the PWM transmitting waveform of c mode corresponding to common-transmitting voltage $V_{common}$.

Figure 4D:
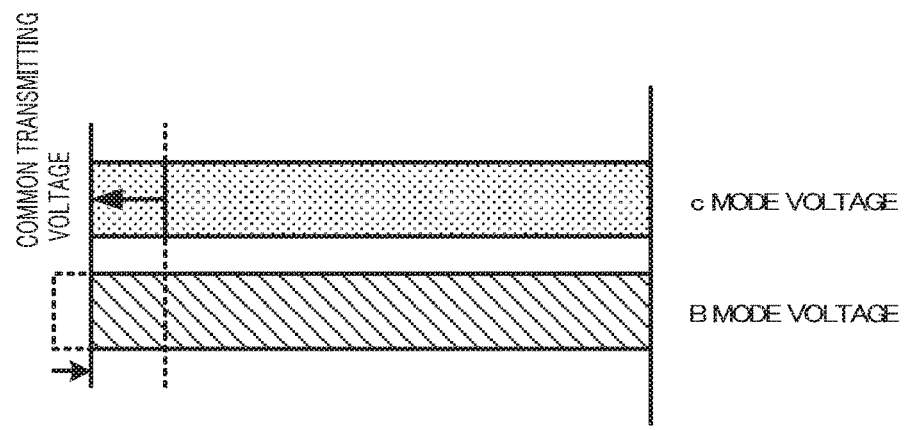
FIG. 4D is a conceptual view illustrating determination of the transmitting voltage by the transmitting-voltage determining section.
Figure 4C:
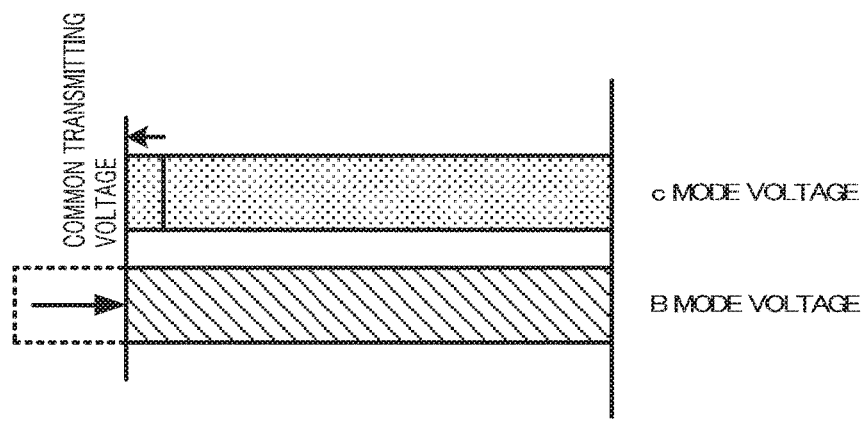
FIG. 4C is a conceptual view illustrating determination of a transmitting voltage by the transmitting-voltage determining section.
Figure 4B:
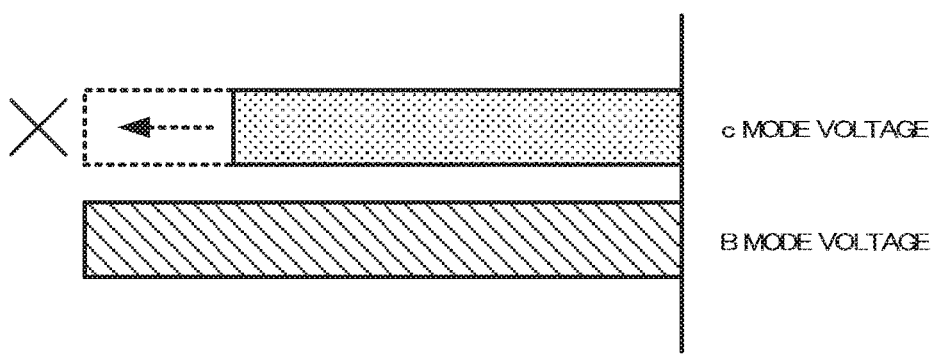
FIG. 4B is a conceptual view illustrating determination of the transmitting voltage by the transmitting-voltage determining section.
Figure 4A:
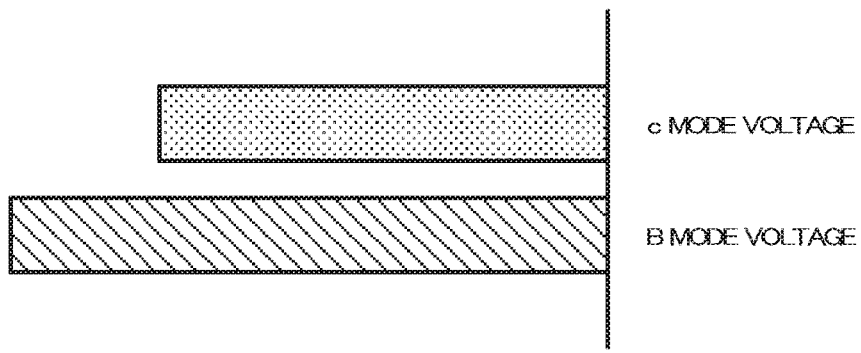
FIG. 4A is a conceptual view illustrating determination of the transmitting voltage by a transmitting-voltage determining section.

FIG. 4A to FIG. 4D are conceptual views of determination of the transmitting voltage by transmitting-voltage determining section 20 described above. FIG. 4A illustrates optimum transmitting voltages of B mode and c mode. It is to be noted that "optimum transmitting voltage" means a high transmitting voltage as possible, with which the acoustic output of the ultrasound waves does not exceed the regulation value of each mode. As illustrated in FIG. 4A, the optimum transmitting voltage of B mode is higher than that of c mode.

FIG. 4B illustrates a case where common-transmitting voltage $V_{common}$ is set to optimum transmitting voltage of B mode (the above-mentioned target voltage $V_T$) so as to handle both of B mode and c mode with a power source of one system. However, since the acoustic output of the ultrasound waves in c mode exceeds the regulation value of c mode, it is not favorable to set common-transmitting voltage $V_{common}$ to target voltage $V_T$.

FIG. 4C illustrates a case where the transmitting voltage of c mode is increased as much as possible while suppressing the acoustic output of the ultrasound waves in c mode to a value equal to or smaller than the regulation value by applying the PWM control in c mode. The voltages of B mode and c mode illustrated in FIG. 4C correspond to intermediate transmitting voltage $V_m$ set at step S311 of FIG. 3.

As illustrated in FIG. 4C, intermediate transmitting voltage $V_m$ is higher than the optimum transmitting voltage of c mode, but lower than target voltage $V_T$ that is optimum transmitting voltage of B mode. Therefore, when intermediate transmitting voltage $V_m$ is set to common-transmitting voltage $V_{common}$, the image quality of B mode might be degraded in comparison with a normal case.

As illustrated in FIG. 4D, degradation in image quality in B mode can be reduced by determining optimum common-transmitting voltage $V_{common}$ by adjusting the transmission interval and the number of transmission of per unit time of B mode and the transmission interval and the transmission frequency per unit time of c mode. The operation of determining the optimum common-transmitting voltage $V_{common}$ described in FIG. 4D corresponds to step S312 of FIG. 3.

In this manner, by determining optimum common-transmitting voltage $V_{common}$ by adjusting the transmission interval and the number of transmission of per unit time of B mode, and the transmission interval and the transmission frequency per unit time of c mode, it is possible to set as high common-transmitting voltage $V_{common}$ as possible with which the acoustic output of the ultrasound waves in each of B mode and c mode does not exceed the regulation value.

While FIG. 4A to FIG. 4D assume a case in which transmitting voltage candidate of c mode is lower than target voltage $V_T$, intermediate transmitting voltage $V_m$ may be set to a lowest voltage in the transmitting voltage candidate of c mode as at step S310 of FIG. 3 when the transmitting voltage candidate of c mode is higher than target voltage $V_T$.

While Bc mode is selected in the Duplex mode in the above description, almost the same operation is executed also when other Duplex modes are selected. To be more specific, while the operation in B mode may be the same as the above-mentioned operation, the operations of pulse-Doppler mode, M mode, E mode and the like may be performed in place of the operation in color-Doppler mode.

<Combined Mode (Triplex Mode)>

Next, an operation of ultrasound diagnostic apparatus 1 in a Triplex mode is described. When a Triplex mode, for example, BcD mode, is selected by operation input section 18, transmitting-voltage determining section 20 sets the transmission condition corresponding to BcD mode. Below, a case where BcD mode is selected as Triplex mode is described.

In BcD mode, as in a single mode and a Duplex mode, transmitting-voltage determining section 20 determines the transmission condition based on transmission information corresponding to B mode, c mode, and pulse-Doppler mode (D-mode) preliminarily stored in transmitting-information storage section 21. At this time, a PWM control is applied to c mode and/or D-mode.

Then, transmission condition setting section 22 sets the transmission condition determined by transmitting-voltage determining section 20, and transmission driving section 12 outputs a driving signal in accordance with the set transmission condition. Here, transmission driving section 12 generates a B mode transmission pulse in the B mode transmission cycle, and a color-Doppler transmission pulse (or a pulse Doppler transmission pulse) in the color Doppler cycle (or pulse Doppler cycle). The transmission condition setting method in the Triplex mode is elaborated later.

Ultrasound probe 30 transmits ultrasound waves based on the driving signal, and receives an echo reflected in a subject. Ultrasound probe 30 generates a reception signal based on the received echo, and outputs the signal to reception signal processing section 13. Reception signal processing section 13 generates a reception signal based on the sound ray data, and outputs the signal to image processing section 16. Image processing section 16 generates an ultrasound image based on the sound ray data. The generated ultrasound image is displayed on display section 19. It is to be noted that transmission/reception switching section 14 appropriately switches output of a driving signal and input of a reception signal between ultrasound diagnostic apparatus main body 10 and ultrasound probe 30.

It is to be noted that the gain of a mode to which the PWM control has not been applied may be compensated when image processing section 16 generates an ultrasound image. To be more specific, in the case where the PWM control has been applied only to D-mode, the gain of B mode and c mode which is low due to employment of a common transmitting voltage can be compensated by multiplying the gain of B mode by (optimum transmitting voltage of B mode)/(common transmitting voltage), and by multiplying the gain of c mode by (the optimum transmitting voltage of c mode)/(common transmitting voltage). While the gains of B mode and c mode are compensated in the above-mentioned example case, only one of them (e.g. only B mode) may be compensated. In addition, in the case where the PWM control has been applied to c mode and D-mode, the gain of B mode which is low due to employment of a common transmitting voltage can be compensated by multiplying the gain of B mode by (optimum transmitting voltage of B mode)/(common transmitting voltage).

Here, as in the case of the combined mode (Duplex mode) described above, it corresponds to addition of a value obtained by converting α-times into decibel (dB) in terms of the gain compensation amount for a signal subjected to a Log-compression, in the case where B mode is high harmonic imaging by THI (Tissue Harmonic Imaging), the gain of B mode may be multiplied by the square of the multiple, and, the gain compensation amount may be determined by other functions in which (optimum transmitting voltage of each mode) and (common transmitting voltage) are the input regardless of whether THI or not.

<Transmission Condition Setting Method (Triplex Mode)>

Now a transmission condition setting method in the Triplex mode is described. It is to be noted that Triplex mode includes a first method in which the PWM control is used for the transmitting voltage control of only one of c mode and D-mode, and a second method in which the PWM control is used in common for c mode and D-mode.

[First Method]

Figure 5:
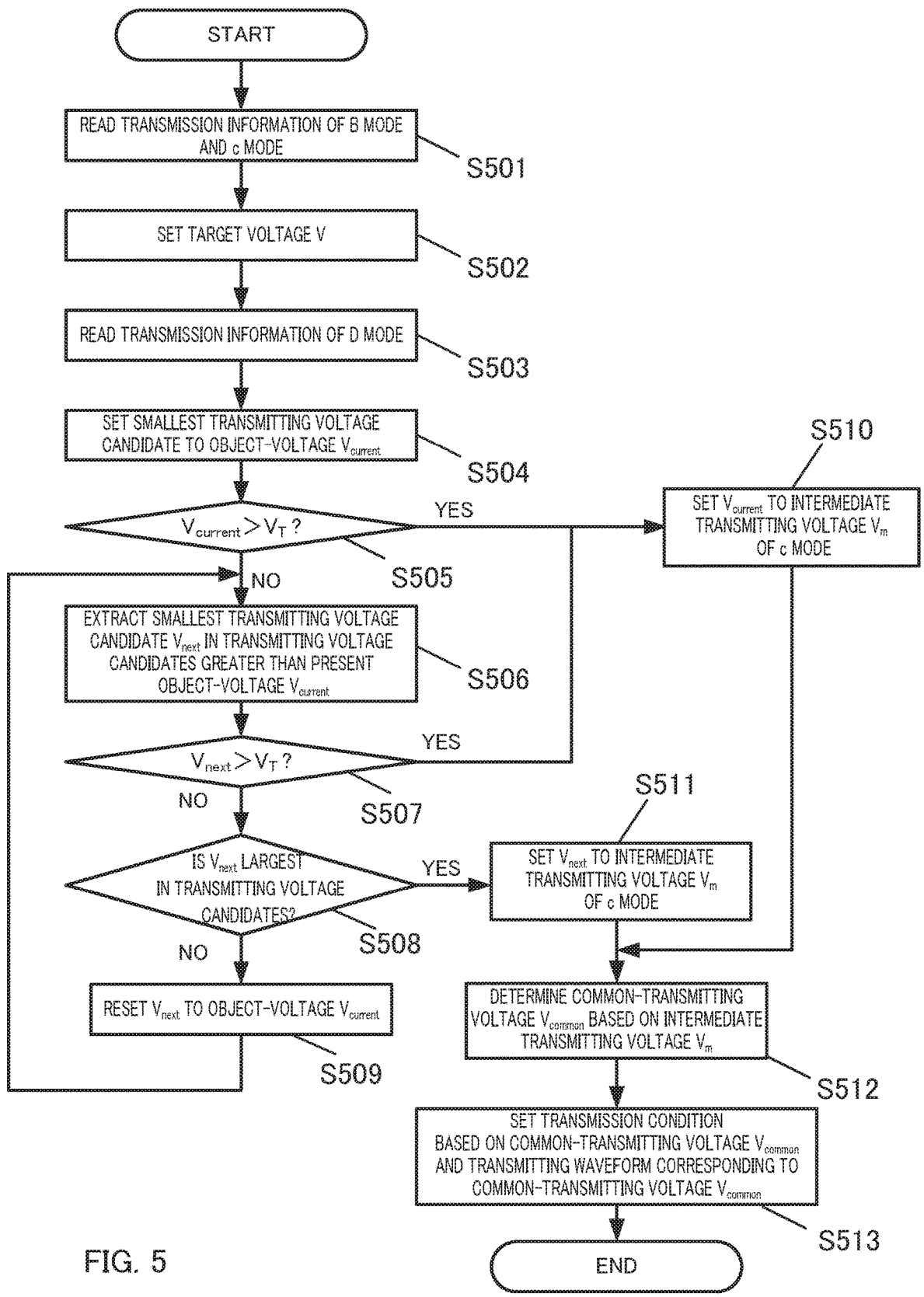
FIG. 5 is a flowchart of a first setting method for a transmission condition in a Triplex mode.

FIG. 5 is a flowchart of a first setting method for the transmission condition in the Triplex mode. In the following description of the first method, the PWM control is applied only for D-mode.

At step S501, transmitting-voltage determining section 20 reads, from transmitting-information storage section 21, transmission information corresponding to B mode and c mode, that is, information containing an optimum transmitting voltage of B mode, a transmitting waveform corresponding to the optimum transmitting voltage of B mode, an optimum transmitting voltage of c mode, and a transmitting waveform corresponding to the optimum transmitting voltage of c mode.

In the above-mentioned transmission condition setting method in the Duplex mode (Bc mode) described in FIG. 3, the PWM control is applied to c mode, and therefore the PWM transmission information corresponding to c mode contains the plurality of transmitting voltage candidates, and PWM waveforms corresponding to the transmitting voltage candidates. In contrast, here, the PWM control is not applied to c mode, and the transmission information corresponding to c mode that is read at step S501 is information that contains the optimum transmitting voltage of c mode, and the transmitting waveform corresponding to the optimum transmitting voltage of c mode. That is, in transmitting-information storage section 21, both the PWM transmission information corresponding to a mode and transmission information corresponding to the mode in the case where the PWM control is not applied are preliminarily stored.

At step S502, transmitting-voltage determining section 20 compares the optimum transmitting voltage in B mode with the optimum transmitting voltage in c mode, and sets the lower transmitting voltage as target voltage $V_T$.

At step S503, transmitting-voltage determining section 20 reads the PWM transmission information corresponding to D-mode from transmitting-information storage section 21. The PWM transmission information corresponding to D-mode contains the plurality of transmitting voltage candidates and the PWM waveforms corresponding to respective transmitting voltage candidates in a table format, for example.

At step S504, transmitting-voltage determining section 20 sets object-voltage $V_{current}$ of the processing object to the smallest transmitting voltage candidate (minimum voltage) in the plurality of transmitting voltage candidates included in transmission information corresponding to D-mode read at step S503.

At step S505, transmitting-voltage determining section 20 compares object-voltage $V_{current}$ and target voltage $V_T$ set at step S502. When object-voltage $V_{current}$ is larger than the other (step S505: YES), the process is advanced to step S510, and when object-voltage $V_{current}$ is not larger than the other (step S505: NO), the process is advanced to step S506.

At step S506, transmitting-voltage determining section 20 extracts the smallest transmitting voltage candidate $V_{next}$ in the transmitting voltage candidates greater than the present object-voltage $V_{current}$ in the plurality of transmitting voltage candidates included in the PWM transmission information corresponding to D-mode read at step S503.

At step S507, transmitting-voltage determining section 20 compares target voltage $V_T$ with $V_{next}$ extracted at step S506. When $V_{next}$ is larger than target voltage $V_T$ (step S507: YES), the process is advanced to step S510, and when $V_{next}$ is not larger than target voltage $V_T$ (step S507: NO), the process is advanced to step S508.

At step S508, transmitting-voltage determining section 20 determines whether $V_{next}$ is the largest transmitting voltage candidate in the plurality of transmitting voltage candidates included in the PWM the transmission information corresponding to c mode read at step S503. When $V_{next}$ is the largest transmitting voltage candidate in the plurality of transmitting voltage candidates (step S508: YES), the process is advanced to step S511, and when $V_{next}$ is not the largest transmitting voltage candidate in the plurality of transmitting voltage candidates (step S508: NO), the process is advanced to step S509.

At step S509, transmitting-voltage determining section 20 resets object-voltage $V_{current}$ to the second smallest transmitting voltage candidate $V_{next}$ that is the smallest except for the present object-voltage $V_{current}$, and then the process is returned to step S506.

At step S510, transmitting-voltage determining section 20 sets $V_{current}$ to intermediate transmitting voltage $V_m$ in D-mode. The intermediate transmitting voltage $V_m$ in D-mode is a temporary transmitting voltage that is used for determining common-transmitting voltage $V_{common}$ in BcD mode.

At step S511, transmitting-voltage determining section 20 sets $V_{next}$ to intermediate transmitting voltage $V_m$ in D-mode.

At step S512, transmitting-voltage determining section 20 determines common-transmitting voltage $V_{common}$ based on target voltage $V_T$ and/or intermediate transmitting voltage $V_m$.

The method of determining common-transmitting voltage $V_{common}$ based on target voltage $V_T$ and/or intermediate transmitting voltage $V_m$ may be the same as that of Duplex mode described at step S312 of FIG. 3.

That is, the first exemplary method is a method in which common-transmitting voltage $V_{common}$ is simply set to smaller one of target voltage $V_T$ and D-mode intermediate transmitting voltage $V_m$. Here, the case where target voltage $V_T$ is smaller corresponds to the case where object-voltage $V_{current}$ is greater than target voltage $V_T$ when compared at step S505. The second exemplary method is a method of optimizing common-transmitting voltage $V_{common}$. The optimization condition is that the acoustic outputs of the ultrasound waves in B mode, c mode and D-mode do no exceed the regulation value of each mode, and that the voltage is as high as possible. This condition is referred to as Condition 2 in the following descriptions.

The common-transmitting voltage $V_{common}$ may be optimized by calculation based on target voltage $V_T$, intermediate transmitting voltage $V_m$, the transmission interval of B mode, c mode and D-mode, the transmission frequency per unit time of B mode, c mode and D-mode and the like, for example. Alternatively, common-transmitting voltage $V_{common}$ may be the largest transmitting voltage in common-transmitting voltages $V_{common}$ meeting Condition 2 determined by searching. Alternatively, common-transmitting voltage $V_{common}$ may be the largest transmitting voltage meeting Condition 2 in possible candidates for transmitting voltage prepared in advance through an experiment and the like and stored in transmitting-information storage section 21 and the like.

Common-transmitting voltage $V_{common}$ that meets Condition 2 can be determined, by searching a parameter where common-transmitting voltage $V_{common}$ is maximized while adjusting the transmission interval and the number of transmission of per unit time of B mode, the transmission interval and the transmission frequency per unit time of c mode, and the transmission interval and the transmission frequency per unit time of D-mode, for example.

The method of determining common-transmitting voltage $V_{common}$ that meets Condition 2 may the same as that of Duplex mode described at step S312 of FIG. 3.

In the Duplex mode, common-transmitting voltage $V_{common}$ is determined by calculating or measuring, with a sensor, the temperature rise at the probe surface in the case where transmission with the waveform of B mode, to which the PWM control is not applied, at the transmitting voltage of B mode and the transmission interval of B mode, and by the transmission frequency per unit time of B mode, and transmission with the PWM waveform of c mode, to which the PWM control is applied, at the transmitting voltage of c mode and the transmission interval of c mode, and by the transmission frequency per unit time of c mode, are repeated. In contrast, in the first method of Triplex mode, common-transmitting voltage $V_{common}$ may be determined by calculating or measuring, with a sensor, the temperature rise at the probe surface in the case where transmission with the waveform of B mode, to which the PWM control is not applied, at the transmitting voltage of B mode and the transmission interval of B mode, and by the transmission frequency per unit time of B mode, transmission with the PWM waveform of c mode, to which the PWM control is not applied, at the transmitting voltage of to c mode and the transmission interval of c mode, and by the transmission frequency per unit time of c mode, and transmission with the PWM waveform of D-mode, to which the PWM control has been applied, at the transmitting voltage of D-mode and transmission interval of D-mode by the transmission frequency per unit time of D-mode, are repeated.

At step S513, transmission condition setting section 22 sets a transmission condition based on common-transmitting voltage $V_{common}$ determined at step S512 and a transmitting waveform corresponding to the common-transmitting voltage $V_{common}$. That is, on the basis of the transmission information of each mode read from transmitting-information storage section 21, transmission condition setting section 22 sets the transmitting waveform in the B mode cycle to the transmitting waveform of B mode corresponding to common-transmitting voltage $V_{common}$, sets the transmitting waveform in the c mode cycle to the transmitting waveform of c mode corresponding to common-transmitting voltage $V_{common}$, and sets the transmitting waveform in D-mode cycle to the PWM transmitting waveform of D-mode corresponding to common-transmitting voltage $V_{common}$.

With this transmission condition setting method, it is possible to set as high common-transmitting voltage $V_{common}$ as possible with which the acoustic output of the ultrasound waves in each of B mode, c mode and D-mode does not exceed the regulation value of each mode.

[Second Method]

Figure 6:
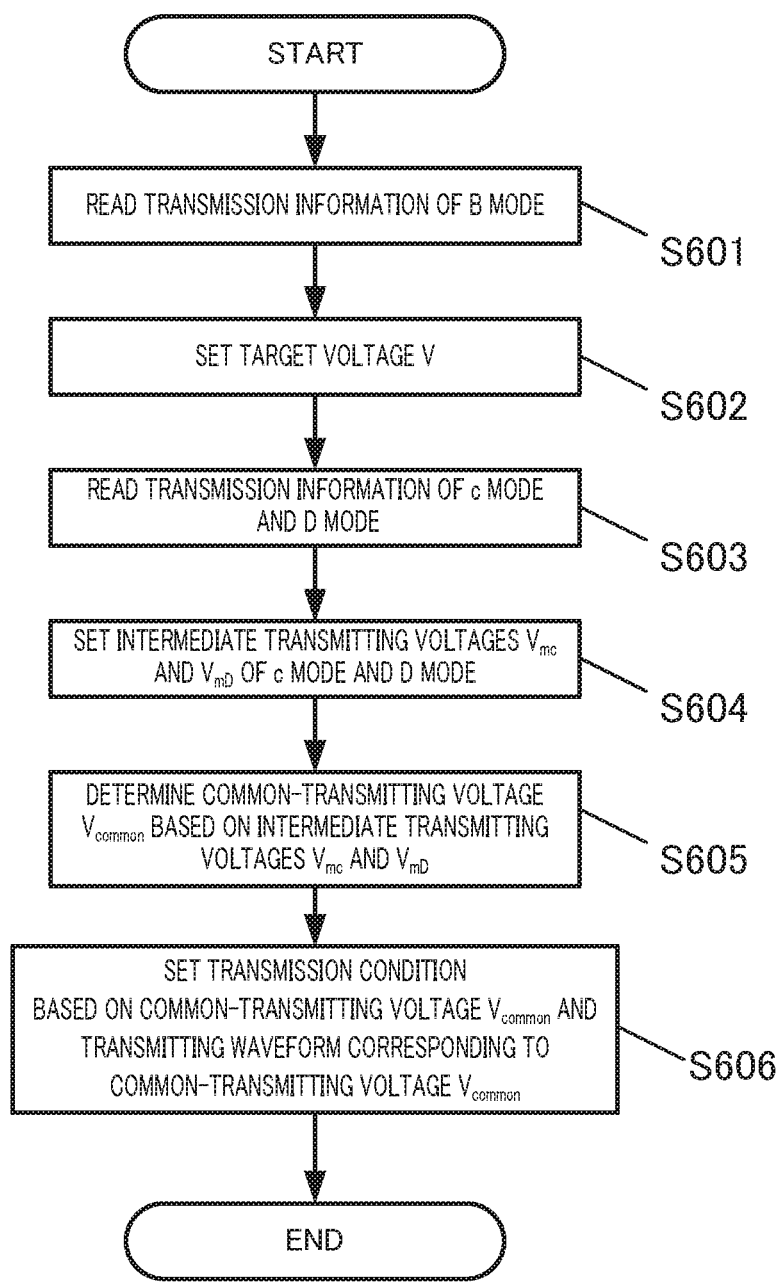
FIG. 6 is a flowchart of a second setting method for a transmission condition in a Triplex mode.

FIG. 6 is a flowchart of a second transmission condition setting method in the Triplex mode. In the following description of the second transmission condition setting method, the PWM control is applied to c mode and D-mode.

At step S601, transmitting-voltage determining section 20 reads transmission information corresponding to B mode, that is, information including the optimum transmitting voltage of B mode, and the transmitting waveform corresponding to the transmitting voltage from transmitting-information storage section 21.

At step S602, transmitting-voltage determining section 20 sets the optimum transmitting voltage in B mode to target voltage $V_T$.

At step S603, transmitting-voltage determining section 20 reads the PWM transmission information corresponding to c mode and the PWM transmission information corresponding to D-mode from transmitting-information storage section 21. Each PWM transmission information contains a plurality of transmitting voltage candidates and PWM waveforms corresponding to respective transmitting voltage candidates in a table format, for example.

At step S604, transmitting-voltage determining section 20 sets intermediate transmitting voltage $V_m$ in c mode c and intermediate transmitting voltage $V_{mD}$ in D-mode. Intermediate transmitting voltage $V_{mc}$ in c mode and intermediate transmitting voltage $V_{mD}$ in D-mode can be set through processes of step S304 to S311 in FIG. 3 (or at steps S504 to S511 in FIG. 5) on each of c mode and D-mode.

At step S605, transmitting-voltage determining section 20 determines common-transmitting voltage $V_{common}$ based on target voltage $V_T$ and/or intermediate transmitting voltages $V_{mc}$ and $V_{mD}$.

Examples of the method of determining common-transmitting voltage $V_{common}$ based on target voltage $V_T$ and/or intermediate transmitting voltages $V_{mc}$ and $V_{mD}$ include the following methods.

Specifically, in the first exemplary method, the smallest voltage among target voltage $V_T$, intermediate transmitting voltage $V_{mc}$ of c mode, and intermediate transmitting voltage $V_{mD}$ of D-mode is set to common-transmitting voltage $V_{common}$.

In the second exemplary method, common-transmitting voltage $V_{common}$ is optimized. The optimization condition is that the acoustic output of the ultrasound waves in each of B mode, c mode and D-mode does not exceed the regulation value of each mode, and that the voltage is as high as possible. This condition is referred to as Condition 3 in the following description.

The common-transmitting voltage $V_{common}$ may be optimized by calculation based on target voltage $V_T$, intermediate transmitting voltages $V_{mc}$ and $V_{mD}$, the transmission interval of B mode, c mode and D-mode, the transmission frequency per unit time of B mode, c mode and D-mode, and the like for example. Alternatively, common-transmitting voltage $V_{common}$ may be the largest transmitting voltage in common-transmitting voltages $V_{common}$ meeting Condition 3 determined by searching. Alternatively, common-transmitting voltage $V_{common}$ may be the largest in transmitting voltage meeting Condition 3 in possible candidates for transmitting voltage prepared in advance through an experiment and the like and stored in transmitting-information storage section 21 and the like.

Common-transmitting voltage $V_{common}$ that meets Condition 3 can be determined by searching a parameter where common-transmitting voltage $V_{common}$ is maximized while adjusting the transmission interval and the number of transmission of per unit time of B mode, the transmission interval and the transmission frequency per unit time of c mode, and the transmission interval and the transmission frequency per unit time of D-mode, for example.

The method of determining common-transmitting voltage $V_{common}$ that meets Condition 3 may the same as that of Duplex mode described at step S312 of FIG. 3.

In the Duplex mode, common-transmitting voltage $V_{common}$ is determined by calculating or measuring, with a sensor, the temperature rise at the probe surface in the case where transmission with the waveform of B mode, to which the PWM control is not applied, at the transmitting voltage of B mode and the transmission interval of B mode, and by the transmission frequency per unit time of B mode, and transmission with the PWM waveform of c mode, to which the PWM control is applied, at the transmitting voltage of c mode and the transmission interval of c mode, and by the transmission frequency per unit time of c mode, are repeated. In contrast, in the second method of Triplex mode, common-transmitting voltage $V_{common}$ may be determined by calculating or measuring, with a sensor, the temperature rise at the probe surface in the case where transmission with the waveform of B mode, to which the PWM control is not applied, at the transmitting voltage of B mode and the transmission interval of B mode, and by the transmission frequency per unit time of B mode, transmission with the PWM waveform of c mode, to which the PWM control is applied, at the transmitting voltage of c mode and the transmission interval of c mode, and by the transmission frequency per unit time of c mode, and transmission with the PWM waveform of D-mode, to which the PWM control has been applied, at the transmitting voltage of D-mode and transmission interval of D-mode by the transmission frequency per unit time of D-mode, are repeated.

At step S606, transmission condition setting section 22 sets a transmission condition based on common-transmitting voltage $V_{common}$ determined at step S605 and the transmitting waveform corresponding to the common-transmitting voltage $V_{common}$. Specifically, on the basis of the transmission information of each mode read from transmitting-information storage section 21, transmission condition setting section 22 sets the transmitting waveform in the B mode cycle to the transmitting waveform of B mode corresponding to common-transmitting voltage $V_{common}$, sets the transmitting waveform in the c mode cycle to the transmitting waveform of c mode corresponding to common-transmitting voltage $V_{common}$, and sets the transmitting waveform in D-mode cycle to the PWM transmitting waveform of D-mode corresponding to common-transmitting voltage $V_{common}$.

With this transmission condition setting method, it is possible to set as high common-transmitting voltage $V_{common}$ as possible the acoustic output of the ultrasound waves in each of B mode, c mode and D-mode does not exceed the regulation value of each mode.

While BcD mode is selected in the above description of Triplex mode, almost the same operation is executed also when other Triplex mode is selected. To be more specific, it suffices to perform an operation such as pulse-Doppler mode, Mc mode, and E-mode instead of the operation in color-Doppler mode, and perform an operation such as color-Doppler mode, Mc mode, E-mode instead of the operation in pulse-Doppler mode with the same operation in B mode as above.

<Operation and Effect>

As described above, ultrasound diagnostic apparatus 1 according to the embodiment of the embodiment of the present invention capable of simultaneously displaying ultrasound images of a plurality of display modes, the ultrasound diagnostic apparatus including a hardware processor configured to: transmitting-information storage section 21 that stores first transmission information in which an optimum transmitting voltage and a transmitting waveform are associated with each other for each display mode, and second transmission information in which a plurality of transmitting voltage candidates and pulse-width modulation transmitting waveforms that are pulse-width-modulation controlled so as to respectively correspond to the plurality of transmitting voltage candidates or a pulse-width modulation ratio that is a ratio of a section whose level is not 0 in a pulse-width modulation transmitting waveform are associated with each other for each display mode; and transmitting-voltage determining section 20 that extracts a maximum transmitting voltage candidate that does not exceed an optimum transmitting voltage of a first display mode of the plurality of display modes from a plurality of transmitting voltage candidates included in the second transmission information of a second display mode of the plurality of display modes so as to determine a common transmitting voltage used in common for the first display mode and the second display mode based on the optimum transmitting voltage of the first display mode and/or the maximum transmitting voltage candidate.

With this configuration, by applying the PWM control to the second display mode, the common transmitting voltage of the first display mode and the second display mode can be set to a high value as much as possible while maintaining the acoustic output of the ultrasound waves in the second display mode at a value equal to or smaller than a regulation value. Thus, the transmitting voltage of two or more display modes can be favorably determined with a power source of one system, and accordingly ultrasound diagnostic apparatus 1 can be downsized while achieving a favorable image quality in each display mode.

In addition, in ultrasound diagnostic apparatus 1 according to the embodiment of the embodiment of the present invention, transmitting-voltage determining section 20 determines the common transmitting voltage based on at least one of an optimum transmitting voltage of the first display mode, the maximum transmitting voltage candidate, transmission intervals of the first display mode and the second display mode, and transmission frequencies of the first display mode and the second display mode per unit time.

With this configuration, the highest common transmitting voltage can be determined based on the transmission interval and the transmission frequency per unit time of the first display mode, and the transmission interval and the transmission frequency per unit time of the second display mode, and thus the transmitting voltage of the second display mode can be set to a high value as much as possible while maintaining the acoustic output of the ultrasound waves in the second display mode at a value equal to or smaller than a regulation value.

In addition, ultrasound diagnostic apparatus 1 according to the embodiment of the embodiment of the present invention further includes transmission condition setting section 22 that sets, as a transmission condition of the first display mode, the common transmitting voltage and the transmitting waveform included in the first transmission information of the first display mode, and, as a transmission condition of the second display mode, the common transmitting voltage and the pulse-width modulation transmitting waveform included in the second transmission information of the second display mode.

With this configuration, it is possible to set a transmission condition based on the transmitting voltage determined by transmitting-voltage determining section 20 and a transmitting waveform corresponding to the transmitting voltage.

In addition, ultrasound diagnostic apparatus 1 according to the embodiment of the embodiment of the present invention transmission further includes image processing section 16 that generates an ultrasound image corresponding to the display mode based on a reception signal generated based on a reflection wave of ultrasound waves sent by a driving signal generated in accordance with a transmission condition set by the transmission condition setter; and image processing section 16 performs gain compensation on the reception signal when generating an ultrasound image corresponding to a display mode in which the common transmitting voltage is lower than the optimum transmitting voltage.

With this configuration, it is possible to compensate the gain of a display mode whose common transmitting voltage is lowered than an optimum transmitting voltage to thereby reduce degradation in image quality.

In addition, in ultrasound diagnostic apparatus 1 according to the embodiment of the embodiment of the present invention, transmitting-voltage determining section 20 extracts a maximum transmitting voltage candidate that does not exceed a transmitting voltage of a lower one of the optimum transmitting voltage of the first display mode of the plurality of display modes and an optimum transmitting voltage of the second display mode of the plurality of display modes from a plurality of transmitting voltage candidates included in the second transmission information of a third display mode of the plurality of display modes so as to determine a common transmitting voltage that is used in common for the first display mode, the second display mode and the third display mode based on at least one of the optimum transmitting voltage of the first display mode, the optimum transmitting voltage of the second display mode, and the maximum transmitting voltage candidate.

In addition, in ultrasound diagnostic apparatus 1 according to the embodiment of the embodiment of the present invention, transmitting-voltage determining section 20 extracts a maximum transmitting voltage candidate that does not exceed an optimum transmitting voltage of the first display mode of the plurality of display modes in a plurality of transmitting voltage candidates included in the second transmission information of the second display mode of the plurality of display modes, extract a maximum transmitting voltage candidate that does not exceed an optimum transmitting voltage of the first display mode of the plurality of display modes in a plurality of transmitting voltage candidates included in the second transmission information of a third display mode of the plurality of display modes, and determine a common transmitting voltage that is used in common for the first display mode, the second display mode and the third display mode based on at least one of the optimum transmitting voltage of the first display mode, the maximum transmitting voltage candidate in the second display mode, and the maximum transmitting voltage candidate in the third display mode.

With this configuration, even in the case where the display of the first to third display modes are simultaneously performed, the common transmitting voltage can be set to be high as much as possible. Thus ultrasound diagnostic apparatus 1 can be downsized while achieving a favorable image quality in each display mode.

While the embodiments of the present invention are described above with reference to the drawings, the present invention is not limited thereto. It should be understood by those skilled in the art that various modifications, combinations, sub-combinations and alterations may occur depending on design requirements and other factors in so far as they are within the scope of the appended claims or the equivalents thereof.

While ultrasound diagnostic apparatus main body 10 includes the control blocks (transmitting-voltage determining section 20, transmitting-information storage section 21, transmission condition setting section 22, transmission driving section 12, reception signal processing section 13, transmission/reception switching section 14, image processing section 16 and the like) which are independent in the present embodiments, the present invention is not limited to this. For example, each control block may be achieved in the form of hardware, or in the form of software. When each control block is achieved in the form of software, a program read by CPU 151 is executed, for example. In addition, a control block in the form of hardware and a control block in the form of software may be combined.

While the single mode, Duplex mode includes two modes, and Triplex mode includes three modes are described in the present embodiment, the present invention is not limited to this. The present invention may be applicable to a mode in which four or more modes are combined, for example.

INDUSTRIAL APPLICABILITY

The present invention is suitable for an ultrasound diagnostic apparatus that can simultaneously display ultrasound images of a plurality of display modes.

Although embodiments of the embodiment of the present invention have been described and illustrated in detail, the disclosed embodiments are made for purposes of illustration and example only and not limitation. The scope of the embodiment of the present invention should be interpreted by terms of the appended claims.

What is claimed is:

1. An ultrasound diagnostic apparatus capable of simultaneously displaying ultrasound images of a plurality of display modes, the ultrasound diagnostic apparatus comprising a hardware processor configured to:

store first transmission information in which an optimum transmitting voltage and a transmitting waveform are associated with each other for at least a first display mode among the plurality of display modes, and second transmission information in which a plurality of transmitting voltage candidates and pulse-width modulation transmitting waveforms that are pulse-width-modulation controlled so as to respectively correspond to the plurality of transmitting voltage candidates or a pulse-width modulation ratio that is a ratio of a section whose level is not 0 in a pulse-width modulation transmitting waveform are associated with each other for at least a second display mode among the plurality of display modes;

iteratively compare the plurality of transmitting voltage candidates included in the second transmission information of the second display mode to the optimum transmitting voltage of the first display mode in order to determine a maximum transmitting voltage candidate among the plurality of transmitting voltage candidates included in the second transmission information of the second display mode that does not exceed the optimum transmitting voltage of the first display mode, to thereby extract the maximum transmitting voltage candidate; and determine a common transmitting voltage used in common for the first display mode and the second display mode based on at least one of the optimum transmitting voltage of the first display mode and the maximum transmitting voltage candidate.

2. The ultrasound diagnostic apparatus according to claim 1, wherein the hardware processor is further configured to:

set the common transmitting voltage and the transmitting waveform included in the first transmission information of the first display mode as a transmission condition of the first display mode; and set the common transmitting voltage and a pulse-width modulation transmitting waveform corresponding to the common transmitting voltage from among the plurality of pulse-width modulation transmitting waveforms included in the second transmission information of the second display mode as a transmission condition of the second display mode.

3. The ultrasound diagnostic apparatus according to claim 1, wherein the hardware processor is further configured to set the maximum transmitting voltage candidate to the common transmitting voltage.

4. The ultrasound diagnostic apparatus according to claim 1, wherein the hardware processor is further configured to determine the common transmitting voltage based on at least one of the optimum transmitting voltage of the first display mode, the maximum transmitting voltage candidate, transmission intervals of the first display mode and the second display mode, and transmission frequencies of the first display mode and the second display mode per unit time.

5. The ultrasound diagnostic apparatus according to claim 1, wherein the hardware processor is further configured to determine the common transmitting voltage by setting a transmission interval of the first display mode, a transmission frequency per unit time of the first display mode, a transmission interval of the second display mode, and a transmission frequency per unit time of the second display mode such that an acoustic output of ultrasound waves transmitted from an ultrasound probe and/or a temperature rise of the ultrasound probe of a case where transmission at the transmission interval of the first display mode and by the transmission frequency per unit time of the first display mode with the common transmitting voltage and a transmitting waveform of the first display mode corresponding to the common transmitting voltage, and transmission at the transmission interval of the second display mode and by the transmission frequency per unit time of the second display mode with the common transmitting voltage and a transmitting waveform of the second display mode corresponding to the common transmitting voltage are repeated with the ultrasound diagnostic apparatus connected with the ultrasound probe does not exceed an acoustic output of ultrasound waves transmitted from the ultrasound probe and/or a temperature rise of the ultrasound probe of a case where transmission at the transmission interval of the first display mode and by the transmission frequency per unit time of the first display mode with the optimum transmitting voltage of the first display mode and a transmitting waveform corresponding to the optimum transmitting voltage, and transmission at the transmission interval of the second display mode and by the transmission frequency per unit time of the second display mode with the maximum transmitting voltage and a transmitting waveform of the second display mode corresponding to the maximum transmitting voltage are repeated with the ultrasound diagnostic apparatus connected with the ultrasound probe.

6. The ultrasound diagnostic apparatus according to claim 1, wherein the hardware processor is further configured to determine the common transmitting voltage based on the optimum transmitting voltage of the first display mode when a minimum transmitting voltage candidate in the plurality of transmitting voltage candidates included in the second transmission information of the second display mode is greater than the optimum transmitting voltage of the first display mode.

7. The ultrasound diagnostic apparatus according to claim 1, wherein the hardware processor is further configured to:
 extract, as the maximum transmitting voltage candidate, a maximum transmitting voltage candidate from among the plurality of transmitting voltage candidates included in the second transmission information for the second display mode that does not exceed a transmitting voltage of a lower one of the optimum transmitting voltage of the first display mode of the plurality of display modes and an optimum transmitting voltage of a third display mode of the plurality of display modes so as to determine, as the common transmitting voltage, a common transmitting voltage that is used in common for the first display mode, the second display mode and the third display mode based on at least one of the optimum transmitting voltage of the first display mode, the optimum transmitting voltage of the third display mode, and the maximum transmitting voltage candidate.

8. The ultrasound diagnostic apparatus according to claim 7, wherein the hardware processor is further configured to:
 store first transmission information in which an optimum transmitting voltage and a transmitting waveform are associated with each other for the third display mode;
 set the common transmitting voltage and the transmitting waveform included in the first transmission information of the first display mode as a transmission condition of the first display mode;
 set the common transmitting voltage and the transmitting waveform included in the first transmission information of the third display mode as a transmission condition of the third display mode; and
 set the common transmitting voltage and a pulse-width modulation transmitting waveform corresponding to the common transmitting voltage from among the plurality of pulse-width modulation transmitting waveforms included in the second transmission information of the second display mode as a transmission condition of the second display mode.

9. The ultrasound diagnostic apparatus according to claim 7, wherein the hardware processor is further configured to set the maximum transmitting voltage candidate to the common transmitting voltage.

10. The ultrasound diagnostic apparatus according to claim 7, wherein the hardware processor is further configured to determine the common transmitting voltage based on at least one of the optimum transmitting voltage of the first display mode, the optimum transmitting voltage of the third display mode, the maximum transmitting voltage candidate, transmission intervals of the first display mode, the second display mode and the third display mode, and transmission frequencies per unit time of the first display mode, the second display mode and the third display mode.

11. The ultrasound diagnostic apparatus according to claim 7, wherein the hardware processor is further configured to determine the common transmitting voltage by setting a transmission interval of the first display mode, a transmission frequency per unit time of the first display mode, a transmission interval of the second display mode, a transmission frequency per unit time of the second display mode, a transmission interval of the third display mode, and a transmission frequency per unit time of the third display mode such that an acoustic output of ultrasound waves transmitted from an ultrasound probe and/or a temperature rise of the ultrasound probe of a case where transmission at the transmission interval of the first display mode and by the transmission frequency per unit time of the first display mode with the common transmitting voltage and a transmitting waveform of the first display mode corresponding to the common transmitting voltage, transmission at the transmission interval of the second display mode and by the transmission frequency per unit time of the second display mode with the common transmitting voltage and a transmitting waveform of the second display mode corresponding to the common transmitting voltage, and transmission at the transmission interval of the third display mode by a transmission frequency per unit time of the third display mode with the common transmitting voltage and a transmitting waveform of the third display mode corresponding to the common transmitting voltage are repeated with the ultrasound diagnostic apparatus connected with the ultrasound probe does not exceed an acoustic output of ultrasound waves transmitted from the ultrasound probe and/or a temperature rise of the ultrasound probe of a case where transmission at the transmission interval of the first display mode and by a transmission frequency per unit time of the first display mode with the optimum transmitting voltage of the first display mode and the transmitting waveform corresponding to the optimum transmitting voltage of the first display mode, transmission at the transmission interval of the third display mode and by the transmission frequency per unit time of the third display mode with the optimum transmitting voltage of the third display mode and a transmitting waveform corresponding to the optimum transmitting voltage of the third display mode, and transmission at the transmission interval of the second display mode and by the transmission frequency per unit time of the second display mode with the maximum transmitting voltage candidate and a transmitting waveform of the second display mode corresponding to the maximum transmitting voltage candidate are repeated with the ultrasound diagnostic apparatus connected with the ultrasound probe.

12. The ultrasound diagnostic apparatus according to claim 1, wherein the hardware processor is further configured to:
   store second transmission information in which a plurality of transmitting voltage candidates and pulse-width modulation transmitting waveforms that are pulse-width-modulation controlled so as to respectively correspond to the plurality of transmitting voltage candidates or a pulse-width modulation ratio that is a ratio of a section whose level is not 0 in a pulse-width modulation transmitting waveform are associated with each other for a third display mode among the plurality of display modes,
   extract a maximum transmitting voltage candidate that does not exceed the optimum transmitting voltage of the first display mode from among the plurality of transmitting voltage candidates included in the second transmission information for the third display mode; and
   determine, as the common transmitting voltage, a common transmitting voltage that is used in common for the first display mode, the second display mode and the third display mode based on at least one of the optimum transmitting voltage of the first display mode, the maximum transmitting voltage candidate in the second display mode, and the maximum transmitting voltage candidate in the third display mode.

13. The ultrasound diagnostic apparatus according to claim 12, wherein the hardware processor is further configured to:
   set the common transmitting voltage and the transmitting waveform included in the first transmission information of the first display mode as a transmission condition of the first display mode;
   set the common transmitting voltage and the pulse-width modulation transmitting waveform included in the second transmission information of the second display mode as a transmission condition of the second display mode; and
   set the common transmitting voltage and the pulse-width modulation transmitting waveform included in the second transmission information of the third display mode as a transmission condition of the third display mode.

14. The ultrasound diagnostic apparatus according to claim 12, wherein the hardware processor is further configured to set the common transmitting voltage to a smaller one of the maximum transmitting voltage candidate in the second display mode, and the maximum transmitting voltage candidate in the third display mode.

15. The ultrasound diagnostic apparatus according to claim 12, wherein the hardware processor is further configured to determine the common transmitting voltage based on at least one of the optimum transmitting voltage of the first display mode, the maximum transmitting voltage candidate in the second display mode, the maximum transmitting voltage candidate in the third display mode, transmission intervals of the first display mode, the second display mode and the third display mode, and transmission frequencies per unit time of the first display mode, the second display mode and the third display mode.

16. The ultrasound diagnostic apparatus according to claim 12, wherein the hardware processor is further configured to determine the common transmitting voltage by setting a transmission interval of the first display mode, a transmission frequency per unit time of the first display mode, a transmission interval of the second display mode, a transmission frequency per unit time of the second display mode, a transmission interval of the third display mode, and a transmission frequency per unit time of the third display mode such that an acoustic output of ultrasound waves transmitted from an ultrasound probe and/or a temperature rise of the ultrasound probe of a case where transmission at the transmission interval of the first display mode and by the transmission frequency per unit time of the first display mode with the common transmitting voltage and a transmitting waveform of the first display mode corresponding to the common transmitting voltage, transmission at the transmission interval of the second display mode and by the transmission frequency per unit time of the second display mode with the common transmitting voltage and a transmitting waveform of the second display mode corresponding to the common transmitting voltage, and transmission at the transmission interval of the third display mode and by the transmission frequency per unit time of the third display mode with the common transmitting voltage and a transmitting waveform of the third display mode corresponding to the common transmitting voltage are repeated with the ultrasound diagnostic apparatus connected with the ultrasound probe, does not exceed an acoustic output of ultrasound waves transmitted from the ultrasound probe and/or a temperature rise of the ultrasound probe of a case where transmission at the transmission interval of the first display mode and by the transmission frequency per unit time of the first display mode with the optimum transmitting voltage of the first display mode and the transmitting waveform corresponding to the optimum transmitting voltage of the first display mode, transmission at the transmission interval of the second display mode and by the transmission frequency per unit time of the second display mode with the maximum transmitting voltage candidate in the second display mode and the transmitting waveform corresponding to the maximum transmitting voltage in the second display mode, transmission at the transmission interval of the third display mode and by the transmission frequency per unit time of the third display mode with the maximum transmitting voltage candidate in the third display mode and a transmitting waveform of the third display mode corresponding to the maximum transmitting voltage candidate in the third display mode are repeated with the ultrasound diagnostic apparatus connected with the ultrasound probe.

17. The ultrasound diagnostic apparatus according to claim 1, wherein the hardware processor is further configured to:
   generate an ultrasound image corresponding to a set display mode among the plurality of display modes based on a reception signal generated based on a reflection wave of ultrasound waves sent by a driving signal generated in accordance with a preset transmission condition; and perform gain compensation on the reception signal when generating, as the ultrasound image, an ultrasound image corresponding to a display mode among the plurality of display modes in which the common transmitting voltage is lower than the optimum transmitting voltage.

18. The ultrasound diagnostic apparatus according to claim 1:
wherein the first display mode is a B mode;
wherein the second display mode is at least one of a color-Doppler mode, a pulse-Doppler mode, an Motion mode, and an Elastography mode;
wherein the plurality of display modes further include a third display mode; and
wherein the third display mode is at least one of the color-Doppler mode, the pulse-Doppler mode, and an Motion+CFM mode, and the third display mode is a different display mode from the second display mode.

19. A transmission condition setting method of an ultrasound diagnostic apparatus capable of simultaneously displaying ultrasound images of a plurality of display modes, the method comprising:
reading first transmission information in which an optimum transmitting voltage and a transmitting waveform are associated with each other, the first transmission information corresponding to a first display mode of the plurality of display modes;
reading second transmission information in which a plurality of transmitting voltage candidates and pulse-width modulation transmitting waveforms that are pulse-width-modulation controlled so as to respectively correspond to the plurality of transmitting voltage candidates or a pulse-width modulation ratio that is a ratio of a section whose level is not 0 in a pulse-width modulation transmitting waveform are associated with each other, the second transmission information corresponding to a second display mode of the plurality of display modes;
iteratively comparing the plurality of transmitting voltage candidates included in the second transmission information of the second display mode to the optimum transmitting voltage of the first display mode in order to determine a maximum transmitting voltage candidate among the plurality of transmitting voltage candidates included in the second transmission information of the second display mode that does not exceed the optimum transmitting voltage of the first display mode, to thereby extract the maximum transmitting voltage candidate; and
determining a common transmitting voltage used in common for the first display mode and the second display mode based on at least one of the optimum transmitting voltage of the first display mode and the maximum transmitting voltage candidate.

20. A non-transitory computer-readable recording medium storing a program configured to be executed by a computer of an ultrasound diagnostic apparatus capable of simultaneously displaying ultrasound images of a plurality of display modes, the program comprising:
reading first transmission information in which an optimum transmitting voltage and a transmitting waveform are associated with each other, the first transmission information corresponding to a first display mode of the plurality of display modes;
reading second transmission information in which a plurality of transmitting voltage candidates and pulse-width modulation transmitting waveforms that are pulse-width-modulation controlled so as to respectively correspond to the plurality of transmitting voltage candidates or a pulse-width modulation ratio that is a ratio of a section whose level is not 0 in a pulse-width modulation transmitting waveform are associated with each other, the second transmission information corresponding to a second display mode of the plurality of display modes;
iteratively comparing the plurality of transmitting voltage candidates included in the second transmission information of the second display mode to the optimum transmitting voltage of the first display mode in order to determine a maximum transmitting voltage candidate among the plurality of transmitting voltage candidates included in the second transmission information of the second display mode that does not exceed the optimum transmitting voltage of the first display mode, to thereby extract the maximum transmitting voltage candidate; and
determining a common transmitting voltage used in common for the first display mode and the second display mode based on at least one of the optimum transmitting voltage of the first display mode and the maximum transmitting voltage candidate.

* * * * *